US009962260B2

(12) United States Patent
Krans et al.

(10) Patent No.: US 9,962,260 B2
(45) Date of Patent: May 8, 2018

(54) PROSTHETIC MITRAL VALVE

(71) Applicant: St. Jude Medical, Cardiology Division, Inc., St. Paul, MN (US)

(72) Inventors: Mark Krans, Hopkins, MN (US); Theodore Paul Dale, Corcoran, MN (US); Andrea N. Para, St. Louis, MO (US); Mathias Charles Glimsdale, St. Michael, MN (US); Thomas M. Benson, Minneapolis, MN (US); Peter N. Braido, Wyoming, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 0 days. days.

(21) Appl. No.: 15/077,070

(22) Filed: Mar. 22, 2016

(65) Prior Publication Data

US 2016/0278923 A1 Sep. 29, 2016

Related U.S. Application Data

(60) Provisional application No. 62/137,444, filed on Mar. 24, 2015.

(51) Int. Cl.
*A61F 2/24* (2006.01)

(52) U.S. Cl.
CPC .......... *A61F 2/2469* (2013.01); *A61F 2/2409* (2013.01); *A61F 2/2418* (2013.01);
(Continued)

(58) Field of Classification Search
CPC .... A61F 2/2469; A61F 2/2409; A61F 2/2418; A61F 2/2445; A61F 2220/0008;
(Continued)

(56) References Cited

U.S. PATENT DOCUMENTS 3,657,744 A 4/1972 Ersek
4,275,469 A 6/1981 Gabbay
(Continued)

FOREIGN PATENT DOCUMENTS

DE 19857887 A1 7/2000
DE 10121210 A1 11/2002
(Continued)

OTHER PUBLICATIONS

International Search Report for International Patent Application PCT/US2016/023510 filed on Mar. 22, 2016.
(Continued)

*Primary Examiner* — Seema Mathew
(74) *Attorney, Agent, or Firm* — Lerner, David, Littenberg, Krumholz & Mentlik, LLP

(57) ABSTRACT

A prosthetic heart valve having an inflow end and an outflow end includes a stent having a collapsed condition, an expanded condition, and a plurality of cells arranged in circumferential rows. The stent may include one or more securement features. One securement feature may be an anchor arm having a body portion and a free end extending from the body portion, the body portion being coupled to a perimeter of one of the plurality of cells, with the free end extending toward the inflow end in an expanded condition of the anchor arm. Another securement feature may include a flange formed of a braided mesh and having a body portion coupled to the stent and a flared portion adjacent the inflow end of the prosthetic heart valve. A valve assembly is disposed within the stent and has a plurality of leaflets.

18 Claims, 31 Drawing Sheets

(52) U.S. Cl.
CPC .... *A61F 2/2445* (2013.01); *A61F 2220/0008* (2013.01); *A61F 2230/0069* (2013.01); *A61F 2250/0069* (2013.01)

(58) Field of Classification Search
CPC ...... A61F 2230/0069; A61F 2250/0069; A61F 2/86; A61F 2/90; A61F 2220/0016; A61F 2/24
See application file for complete search history.

(56) References Cited

U.S. PATENT DOCUMENTS

| | | |
|---|---|---|
| 4,491,986 A | 1/1985 | Gabbay |
| 4,759,758 A | 7/1988 | Gabbay |
| 4,878,906 A | 11/1989 | Lindemann et al. |
| 4,922,905 A | 5/1990 | Strecker |
| 4,994,077 A | 2/1991 | Dobben |
| 5,411,552 A | 5/1995 | Andersen et al. |
| 5,415,664 A | 5/1995 | Pinchuk |
| 5,480,423 A | 1/1996 | Ravenscroft et al. |
| 5,540,712 A * | 7/1996 | Kleshinski ............... A61F 2/90 606/198 |
| 5,843,167 A | 12/1998 | Dwyer et al. |
| 5,855,601 A | 1/1999 | Bessler et al. |
| 5,935,163 A | 8/1999 | Gabbay |
| 5,961,549 A | 10/1999 | Nguyen et al. |
| 6,045,576 A | 4/2000 | Starr et al. |
| 6,077,297 A | 6/2000 | Robinson et al. |
| 6,083,257 A | 7/2000 | Taylor et al. |
| 6,090,140 A | 7/2000 | Gabbay |
| 6,214,036 B1 | 4/2001 | Letendre et al. |
| 6,264,691 B1 | 7/2001 | Gabbay |
| 6,267,783 B1 | 7/2001 | Letendre et al. |
| 6,368,348 B1 | 4/2002 | Gabbay |
| 6,419,695 B1 | 7/2002 | Gabbay |
| 6,458,153 B1 | 10/2002 | Bailey et al. |
| 6,468,660 B2 | 10/2002 | Ogle et al. |
| 6,488,702 B1 | 12/2002 | Besselink |
| 6,517,576 B2 | 2/2003 | Gabbay |
| 6,533,810 B2 | 3/2003 | Hankh et al. |
| 6,582,464 B2 | 6/2003 | Gabbay |
| 6,610,088 B1 | 8/2003 | Gabbay |
| 6,623,518 B2 | 9/2003 | Thompson et al. |
| 6,652,578 B2 | 11/2003 | Bailey et al. |
| 6,685,625 B2 | 2/2004 | Gabbay |
| 6,716,244 B2 | 4/2004 | Klaco |
| 6,719,789 B2 | 4/2004 | Cox |
| 6,730,118 B2 | 5/2004 | Spenser et al. |
| 6,783,556 B1 | 8/2004 | Gabbay |
| 6,790,230 B2 | 9/2004 | Beyersdorf et al. |
| 6,814,746 B2 | 11/2004 | Thompson et al. |
| 6,830,584 B1 | 12/2004 | Seguin |
| 6,869,444 B2 | 3/2005 | Gabbay |
| 6,893,460 B2 | 5/2005 | Spenser et al. |
| 6,908,481 B2 | 6/2005 | Cribier |
| 6,951,573 B1 | 10/2005 | Dilling |
| 7,018,406 B2 | 3/2006 | Seguin et al. |
| 7,025,780 B2 | 4/2006 | Gabbay |
| 7,137,184 B2 | 11/2006 | Schreck |
| 7,160,322 B2 | 1/2007 | Gabbay |
| 7,195,641 B2 | 3/2007 | Palmaz et al. |
| 7,247,167 B2 | 7/2007 | Gabbay |
| 7,267,686 B2 | 9/2007 | DiMatteo et al. |
| 7,276,078 B2 | 10/2007 | Spenser et al. |
| 7,311,730 B2 | 12/2007 | Gabbay |
| 7,320,704 B2 | 1/2008 | Lashinski et al. |
| 7,329,278 B2 | 2/2008 | Seguin et al. |
| 7,374,573 B2 | 5/2008 | Gabbay |
| 7,381,218 B2 | 6/2008 | Schreck |
| 7,381,219 B2 | 6/2008 | Salahieh et al. |
| 7,452,371 B2 | 11/2008 | Pavcnik et al. |
| 7,510,572 B2 | 3/2009 | Gabbay |
| 7,510,575 B2 | 3/2009 | Spenser et al. |
| 7,524,331 B2 | 4/2009 | Birdsall |
| 7,534,261 B2 | 5/2009 | Friedman |
| RE40,816 E | 6/2009 | Taylor et al. |
| 7,585,321 B2 | 9/2009 | Cribier |
| 7,628,805 B2 | 12/2009 | Spenser et al. |
| 7,682,390 B2 | 3/2010 | Seguin |
| 7,708,775 B2 | 5/2010 | Rowe et al. |
| 7,731,742 B2 | 6/2010 | Schlick et al. |
| 7,748,389 B2 | 7/2010 | Salahieh et al. |
| 7,780,725 B2 | 8/2010 | Haug et al. |
| 7,799,069 B2 | 9/2010 | Bailey et al. |
| 7,803,185 B2 | 9/2010 | Gabbay |
| 7,824,442 B2 | 11/2010 | Salahieh et al. |
| 7,837,727 B2 | 11/2010 | Goetz et al. |
| 7,846,203 B2 | 12/2010 | Cribier |
| 7,846,204 B2 | 12/2010 | Letac et al. |
| 7,892,281 B2 | 2/2011 | Seguin et al. |
| 7,914,569 B2 | 3/2011 | Nguyen et al. |
| 7,959,666 B2 | 6/2011 | Salahieh et al. |
| 7,959,672 B2 | 6/2011 | Salahieh et al. |
| 7,972,378 B2 | 7/2011 | Tabor et al. |
| 7,988,724 B2 | 8/2011 | Salahieh et al. |
| 7,993,394 B2 | 8/2011 | Hariton et al. |
| 8,016,877 B2 | 9/2011 | Seguin et al. |
| D648,854 S | 11/2011 | Braido |
| 8,048,153 B2 | 11/2011 | Salahieh et al. |
| 8,052,741 B2 | 11/2011 | Bruszewski et al. |
| 8,052,749 B2 | 11/2011 | Salahieh et al. |
| 8,052,750 B2 | 11/2011 | Tuval et al. |
| 8,062,355 B2 | 11/2011 | Figulla et al. |
| 8,075,611 B2 | 12/2011 | Millwee et al. |
| D652,926 S | 1/2012 | Braido |
| D652,927 S | 1/2012 | Braido et al. |
| D653,341 S | 1/2012 | Braido et al. |
| D653,342 S | 1/2012 | Braido et al. |
| D653,343 S | 1/2012 | Ness et al. |
| D654,169 S | 2/2012 | Braido |
| D654,170 S | 2/2012 | Braido et al. |
| 8,137,398 B2 | 3/2012 | Tuval et al. |
| 8,142,497 B2 | 3/2012 | Friedman |
| D660,432 S | 5/2012 | Braido |
| D660,433 S | 5/2012 | Braido et al. |
| D660,967 S | 5/2012 | Braido et al. |
| 8,182,528 B2 | 5/2012 | Salahieh et al. |
| 8,221,493 B2 | 7/2012 | Boyle et al. |
| 8,230,717 B2 | 7/2012 | Matonick |
| 8,231,670 B2 | 7/2012 | Salahieh et al. |
| 8,252,051 B2 | 8/2012 | Chau et al. |
| 8,308,798 B2 | 11/2012 | Pintor et al. |
| 8,313,525 B2 | 11/2012 | Tuval et al. |
| 8,323,335 B2 | 12/2012 | Rowe et al. |
| 8,323,336 B2 | 12/2012 | Hill et al. |
| 8,343,213 B2 | 1/2013 | Salahieh et al. |
| 8,348,995 B2 | 1/2013 | Tuval et al. |
| 8,348,996 B2 | 1/2013 | Tuval et al. |
| 8,348,998 B2 | 1/2013 | Pintor et al. |
| 8,366,769 B2 | 2/2013 | Huynh et al. |
| 8,403,983 B2 | 3/2013 | Quadri et al. |
| 8,408,214 B2 | 4/2013 | Spenser |
| 8,414,643 B2 | 4/2013 | Tuval et al. |
| 8,425,593 B2 | 4/2013 | Braido et al. |
| 8,449,599 B2 | 5/2013 | Chau et al. |
| 8,449,604 B2 | 5/2013 | Moaddeb et al. |
| 8,454,686 B2 | 6/2013 | Alkhatib |
| 8,500,798 B2 | 8/2013 | Rowe et al. |
| 8,568,474 B2 | 10/2013 | Yeung et al. |
| 8,579,962 B2 | 11/2013 | Salahieh et al. |
| 8,579,966 B2 | 11/2013 | Seguin et al. |
| 8,585,755 B2 | 11/2013 | Chau et al. |
| 8,591,575 B2 | 11/2013 | Cribier |
| 8,597,349 B2 | 12/2013 | Alkhatib |
| 8,603,159 B2 | 12/2013 | Seguin et al. |
| 8,603,160 B2 | 12/2013 | Salahieh et al. |
| 8,613,765 B2 | 12/2013 | Bonhoeffer et al. |
| 8,623,074 B2 | 1/2014 | Ryan |
| 8,652,204 B2 | 2/2014 | Quill et al. |
| 8,663,322 B2 | 3/2014 | Keranen |
| 8,668,733 B2 | 3/2014 | Haug et al. |
| 8,685,080 B2 | 4/2014 | White |
| 8,685,086 B2 * | 4/2014 | Navia ................... A61F 2/2418 623/2.14 |

(56) References Cited

U.S. PATENT DOCUMENTS

| | | | |
|---|---|---|---|
| 8,728,154 B2 | 5/2014 | Alkhatib | |
| 8,747,459 B2 | 6/2014 | Nguyen et al. | |
| 8,764,820 B2 | 7/2014 | Dehdashtian et al. | |
| 8,795,357 B2 | 8/2014 | Yohanan et al. | |
| 8,801,776 B2 | 8/2014 | House et al. | |
| 8,808,356 B2 | 8/2014 | Braido et al. | |
| 8,828,078 B2 | 9/2014 | Salahieh et al. | |
| 8,834,563 B2 | 9/2014 | Righini | |
| 8,840,663 B2 | 9/2014 | Salahieh et al. | |
| 8,876,894 B2 | 11/2014 | Tuval et al. | |
| 8,876,895 B2 | 11/2014 | Tuval et al. | |
| 8,940,040 B2 | 1/2015 | Shahriari | |
| 8,945,209 B2 | 2/2015 | Bonyuet et al. | |
| 8,961,595 B2 | 2/2015 | Alkhatib | |
| 8,974,523 B2 | 3/2015 | Thill et al. | |
| 8,974,524 B2 | 3/2015 | Yeung et al. | |
| 9,358,108 B2 * | 6/2016 | Bortlein | A61F 2/2418 |
| 9,610,159 B2 * | 4/2017 | Christianson | A61F 2/2418 |
| 9,782,256 B2 * | 10/2017 | Zeng | A61F 2/2418 |
| 2002/0036220 A1 | 3/2002 | Gabbay | |
| 2003/0023303 A1 | 1/2003 | Palmaz et al. | |
| 2003/0050694 A1 | 3/2003 | Yang et al. | |
| 2003/0130726 A1 | 7/2003 | Thorpe et al. | |
| 2004/0049262 A1 | 3/2004 | Obermiller et al. | |
| 2004/0093075 A1 | 5/2004 | Kuehne | |
| 2004/0111111 A1 | 6/2004 | Lin | |
| 2004/0210304 A1 | 10/2004 | Seguin et al. | |
| 2004/0260389 A1 | 12/2004 | Case et al. | |
| 2005/0096726 A1 | 5/2005 | Sequin et al. | |
| 2005/0137682 A1 | 6/2005 | Justino | |
| 2005/0137695 A1 | 6/2005 | Salahieh et al. | |
| 2005/0137697 A1 | 6/2005 | Salahieh et al. | |
| 2005/0203605 A1 | 9/2005 | Dolan | |
| 2005/0240200 A1 | 10/2005 | Bergheim | |
| 2005/0256566 A1 | 11/2005 | Gabbay | |
| 2006/0008497 A1 | 1/2006 | Gabbay | |
| 2006/0074484 A1 | 4/2006 | Huber | |
| 2006/0122692 A1 | 6/2006 | Gilad et al. | |
| 2006/0149360 A1 | 7/2006 | Schwammenthal et al. | |
| 2006/0161249 A1 | 7/2006 | Realyvasquez et al. | |
| 2006/0173532 A1 | 8/2006 | Flagle et al. | |
| 2006/0178740 A1 | 8/2006 | Stacchino et al. | |
| 2006/0195180 A1 | 8/2006 | Kheradvar et al. | |
| 2006/0206202 A1 | 9/2006 | Bonhoeffer et al. | |
| 2006/0241744 A1 | 10/2006 | Beith | |
| 2006/0241745 A1 | 10/2006 | Solem | |
| 2006/0259120 A1 | 11/2006 | Vongphakdy et al. | |
| 2006/0259137 A1 | 11/2006 | Artof et al. | |
| 2006/0265056 A1 | 11/2006 | Nguyen et al. | |
| 2006/0276813 A1 | 12/2006 | Greenberg | |
| 2006/0276874 A1 | 12/2006 | Wilson et al. | |
| 2007/0010876 A1 | 1/2007 | Salahieh et al. | |
| 2007/0027534 A1 | 2/2007 | Bergheim et al. | |
| 2007/0043435 A1 | 2/2007 | Seguin et al. | |
| 2007/0055358 A1 | 3/2007 | Krolik et al. | |
| 2007/0067029 A1 | 3/2007 | Gabbay | |
| 2007/0093890 A1 | 4/2007 | Eliasen et al. | |
| 2007/0100435 A1 | 5/2007 | Case et al. | |
| 2007/0118210 A1 | 5/2007 | Pinchuk | |
| 2007/0213813 A1 | 9/2007 | Von Segesser et al. | |
| 2007/0233228 A1 | 10/2007 | Eberhardt et al. | |
| 2007/0244545 A1 | 10/2007 | Birdsall et al. | |
| 2007/0244552 A1 | 10/2007 | Salahieh et al. | |
| 2007/0288087 A1 | 12/2007 | Fearnot et al. | |
| 2008/0021552 A1 | 1/2008 | Gabbay | |
| 2008/0039934 A1 | 2/2008 | Styrc | |
| 2008/0071369 A1 | 3/2008 | Tuval et al. | |
| 2008/0082164 A1 | 4/2008 | Friedman | |
| 2008/0097595 A1 | 4/2008 | Gabbay | |
| 2008/0114452 A1 | 5/2008 | Gabbay | |
| 2008/0125853 A1 | 5/2008 | Bailey et al. | |
| 2008/0140189 A1 | 6/2008 | Nguyen et al. | |
| 2008/0147183 A1 | 6/2008 | Styrc | |
| 2008/0154355 A1 | 6/2008 | Benichou et al. | |
| 2008/0154356 A1 | 6/2008 | Obermiller et al. | |
| 2008/0243245 A1 | 10/2008 | Thambar et al. | |
| 2008/0255662 A1 | 10/2008 | Stacchino et al. | |
| 2008/0262602 A1 | 10/2008 | Wilk et al. | |
| 2008/0269879 A1 | 10/2008 | Sathe et al. | |
| 2009/0099653 A1 | 4/2009 | Suri et al. | |
| 2009/0112309 A1 | 4/2009 | Jaramillo et al. | |
| 2009/0138079 A1 | 5/2009 | Tuval et al. | |
| 2009/0276027 A1 | 11/2009 | Glynn | |
| 2010/0004740 A1 | 1/2010 | Seguin et al. | |
| 2010/0036484 A1 | 2/2010 | Hariton et al. | |
| 2010/0049306 A1 | 2/2010 | House et al. | |
| 2010/0087907 A1 | 4/2010 | Lattouf | |
| 2010/0131055 A1 | 5/2010 | Case et al. | |
| 2010/0168778 A1 | 7/2010 | Braido | |
| 2010/0168839 A1 | 7/2010 | Braido et al. | |
| 2010/0168844 A1 | 7/2010 | Toomes et al. | |
| 2010/0185277 A1 | 7/2010 | Braido et al. | |
| 2010/0191326 A1 | 7/2010 | Alkhatib | |
| 2010/0204781 A1 | 8/2010 | Alkhatib | |
| 2010/0204785 A1 | 8/2010 | Alkhatib | |
| 2010/0217382 A1 | 8/2010 | Chau et al. | |
| 2010/0234940 A1 | 9/2010 | Dolan | |
| 2010/0249911 A1 | 9/2010 | Alkhatib | |
| 2010/0249923 A1 | 9/2010 | Alkhatib et al. | |
| 2010/0286768 A1 | 11/2010 | Alkhatib | |
| 2010/0298931 A1 | 11/2010 | Quadri et al. | |
| 2011/0029072 A1 | 2/2011 | Gabbay | |
| 2011/0054466 A1 | 3/2011 | Rothstein et al. | |
| 2011/0098800 A1 | 4/2011 | Braido et al. | |
| 2011/0098802 A1 | 4/2011 | Braido et al. | |
| 2011/0137397 A1 | 6/2011 | Chau et al. | |
| 2011/0172765 A1 | 7/2011 | Nguyen et al. | |
| 2011/0208283 A1 | 8/2011 | Rust | |
| 2011/0264206 A1 | 10/2011 | Tabor | |
| 2012/0022640 A1 * | 1/2012 | Gross | A61B 17/068 623/2.11 |
| 2012/0035722 A1 | 2/2012 | Tuval | |
| 2012/0078347 A1 | 3/2012 | Braido et al. | |
| 2012/0101572 A1 | 4/2012 | Kovalsky et al. | |
| 2012/0123529 A1 | 5/2012 | Levi et al. | |
| 2012/0271403 A1 * | 10/2012 | Gries | D04C 1/06 623/1.15 |
| 2012/0303116 A1 | 11/2012 | Gorman, III et al. | |
| 2013/0274873 A1 | 10/2013 | Delaloye et al. | |
| 2014/0121763 A1 | 5/2014 | Duffy et al. | |
| 2014/0155997 A1 | 6/2014 | Braido | |
| 2014/0214159 A1 | 7/2014 | Vidlund et al. | |
| 2014/0222136 A1 * | 8/2014 | Geist | A61F 2/2466 623/2.11 |
| 2014/0228946 A1 | 8/2014 | Chau et al. | |
| 2014/0236292 A1 | 8/2014 | Braido | |
| 2014/0277411 A1 | 9/2014 | Bortlein et al. | |
| 2014/0277422 A1 * | 9/2014 | Ratz | A61F 2/2418 623/2.37 |
| 2014/0303719 A1 * | 10/2014 | Cox | A61F 2/2418 623/2.11 |
| 2014/0324164 A1 | 10/2014 | Gross et al. | |
| 2014/0330371 A1 * | 11/2014 | Gloss | A61F 2/2418 623/2.17 |
| 2014/0343671 A1 | 11/2014 | Yohanan et al. | |
| 2014/0350668 A1 | 11/2014 | Delaloye et al. | |
| 2014/0350669 A1 | 11/2014 | Gillespie et al. | |
| 2014/0371844 A1 | 12/2014 | Dale et al. | |
| 2015/0359631 A1 * | 12/2015 | Sheahan | A61F 2/2418 623/2.19 |
| 2016/0310267 A1 * | 10/2016 | Zeng | A61F 2/2418 |
| 2018/0021131 A1 * | 1/2018 | Zeng | A61F 2/24 |

FOREIGN PATENT DOCUMENTS

| | | |
|---|---|---|
| DE | 102005003632 A1 | 8/2006 |
| DE | 202008009610 U1 | 12/2008 |
| EP | 537487 A1 | 4/1993 |
| EP | 0850607 A1 | 7/1998 |
| EP | 1000590 A1 | 5/2000 |
| EP | 1360942 A1 | 11/2003 |
| EP | 1584306 A1 | 10/2005 |
| EP | 1598031 A2 | 11/2005 |

(56) References Cited

FOREIGN PATENT DOCUMENTS

| | | | |
|---|---|---|---|
| EP | 1926455 A2 | 6/2008 | |
| FR | 2847800 A1 | 6/2004 | |
| FR | 2850008 A1 | 7/2004 | |
| WO | 9117720 A1 | 11/1991 | |
| WO | 9716133 A1 | 5/1997 | |
| WO | 9832412 A2 | 7/1998 | |
| WO | 9913801 A1 | 3/1999 | |
| WO | 01/028459 A1 | 4/2001 | |
| WO | 0149213 A2 | 7/2001 | |
| WO | 01054625 A1 | 8/2001 | |
| WO | 01056500 A2 | 8/2001 | |
| WO | 01076510 A2 | 10/2001 | |
| WO | 0236048 A1 | 5/2002 | |
| WO | 0247575 A2 | 6/2002 | |
| WO | 02067782 A2 | 9/2002 | |
| WO | 03047468 A1 | 6/2003 | |
| WO | 2005070343 A1 | 8/2005 | |
| WO | 06073626 A2 | 7/2006 | |
| WO | 07071436 A2 | 6/2007 | |
| WO | 08070797 A2 | 6/2008 | |
| WO | 10008548 A2 | 1/2010 | |
| WO | 10008549 A1 | 1/2010 | |
| WO | 10096176 A1 | 8/2010 | |
| WO | 10098857 A1 | 9/2010 | |
| WO | 2015142648 | 9/2015 | |
| WO | WO 2015142648 A1 * | 9/2015 | ........... A61F 2/2418 |

OTHER PUBLICATIONS

Ruiz, Carlos, Overview of PRE-CE Mark Transcatheter Aortic Valve Technologies, Euro PCR, dated May 25, 2010.
Percutaneous aortic valve replacement: resection before implantation, 836-840, Quaden, Rene et al., European J. of Cardio-thoracic Surgery, 27 (2005).
Catheter-implanted prosthetic heart valves, Knudsen, L.L., et al., The International Journal of Artificial Organs, vol. 16, No. 5 1993, pp. 253-262.
Transluminal Aortic Valve Placement, Moazami, Nader, et al., ASAIO Journal, 1996; 42:M381-M385.
Transluminal Catheter Implanted Prosthetic Heart Valves, Andersen, Henning Rud, International Journal of Angiology 7:102-106 (1998).
Transluminal implantation of artificial heart valves, Andersen, H. R., et al., European Heart Journal (1992) 13, 704-708.
Is It Reasonable to Treat All Calcified Stenotic Aortic Valves With a Valved Stent?, 579-584, Zegdi, Rachid, MD, PhD et al., J. of the American College of Cardiology, vol. 51, No. 5, Feb. 5, 2008.
"Direct-Access Valve Replacement", Christoph H. Huber, et al., Journal of the American College of Cardiology, vol. 46, No. 2, (Jul. 19, 2005).
"Percutaneous Aortic Valve Implantation Retrograde From the Femoral Artery", John G. Webb et al., Circulation, 2006; 113:842-850 (Feb. 6, 2006).
"Minimally invasive cardiac surgery", M. J. Mack, Surgical Endoscopy, 2006, 20:S488-S492, DOI: 10.1007/s00464-006-0110-8 (presented Apr. 24, 2006).
"Transapical Transcatheter Aortic Valve Implantation in Humans", Samuel V. Lichtenstein et al., Circulation. 2006; 114: 591-596 (Jul. 31, 2006).
"Closed heart surgery: Back to the future", Samuel V. Lichtenstein, The Journal of Thoracic and Cardiovascular Surgery, vol. 131, No. 5, pp. 941-943.
"Transapical approach for sutureless stent-fixed aortic valve implantation: experimental results"; Th. Walther et al., European Journal of Cardio-thoracic Surgery 29 (2006) 703-708 (Jan. 30, 2006).
"Transapical aortic valve implantation: an animal feasibility study"; Todd M. Dewey et al., The annals of thoracic surgery 2006; 82: 110-6 (Feb. 13, 2006).
Textbook "Transcatheter Valve Repair", 2006, pp. 165-186.
Rohde, I., Masch, J.-M., Theisen-Kunde, D., Marczynski-Bühlow, M., Bombien Quaden, R., Lutter, G. and Brinkmann, R. (2015), Resection of Calcified Aortic Heart Leaflets in Vitro by Q-Switched 2 μm Microsecond Laser Radiation. Journal of Cardiac Surgery, 30: 157-162. doi: 10.1111/jocs.12481.
U.S. Appl. No. 29/375,243, filed Sep. 20, 2010.
U.S. Appl. No. 29/375,260, filed Sep. 20, 2010.
Muñoz, Daniel Rodríguez, Carla Lázaro Rivera, and José Luis Zamorano Gómez. "Guidance of treatment of perivalvular prosthetic leaks." Current cardiology reports 16.1 (2014): 1-6.
Gössl, Mario, and Charanjit S. Rihal. "Percutaneous treatment of aortic and mitral valve paravalvular regurgitation." Current cardiology reports 15.8 (2013): 1-8.
Swiatkiewicz, Iwona, et al. "Percutaneous closure of mitral perivalvular leak." Kardiologia polska 67.7 (2009): 762.
De Cicco, Giuseppe, et al. "Aortic valve periprosthetic leakage: anatomic observations and surgical results." The Annals of thoracic surgery 79.5 (2005): 1480-1485.
Heat Advisor, "Heart repairs without surgery. Minimally invasive procedures aim to correct valve leakage", Sep. 2004, PubMed ID 15586429.
Transcatheter Umbrella Closure of Valvular and Paravalvular Leaks, Hourihan et al., Journal of the American College of Cardiology, vol. 20, No. 6, pp. 1371-1377, (1992).
Buellesfeld et al., Treatment of paravalvular leaks through inverventional techniques; Department of Cardiology, Ben University Hospital 2011.

\* cited by examiner

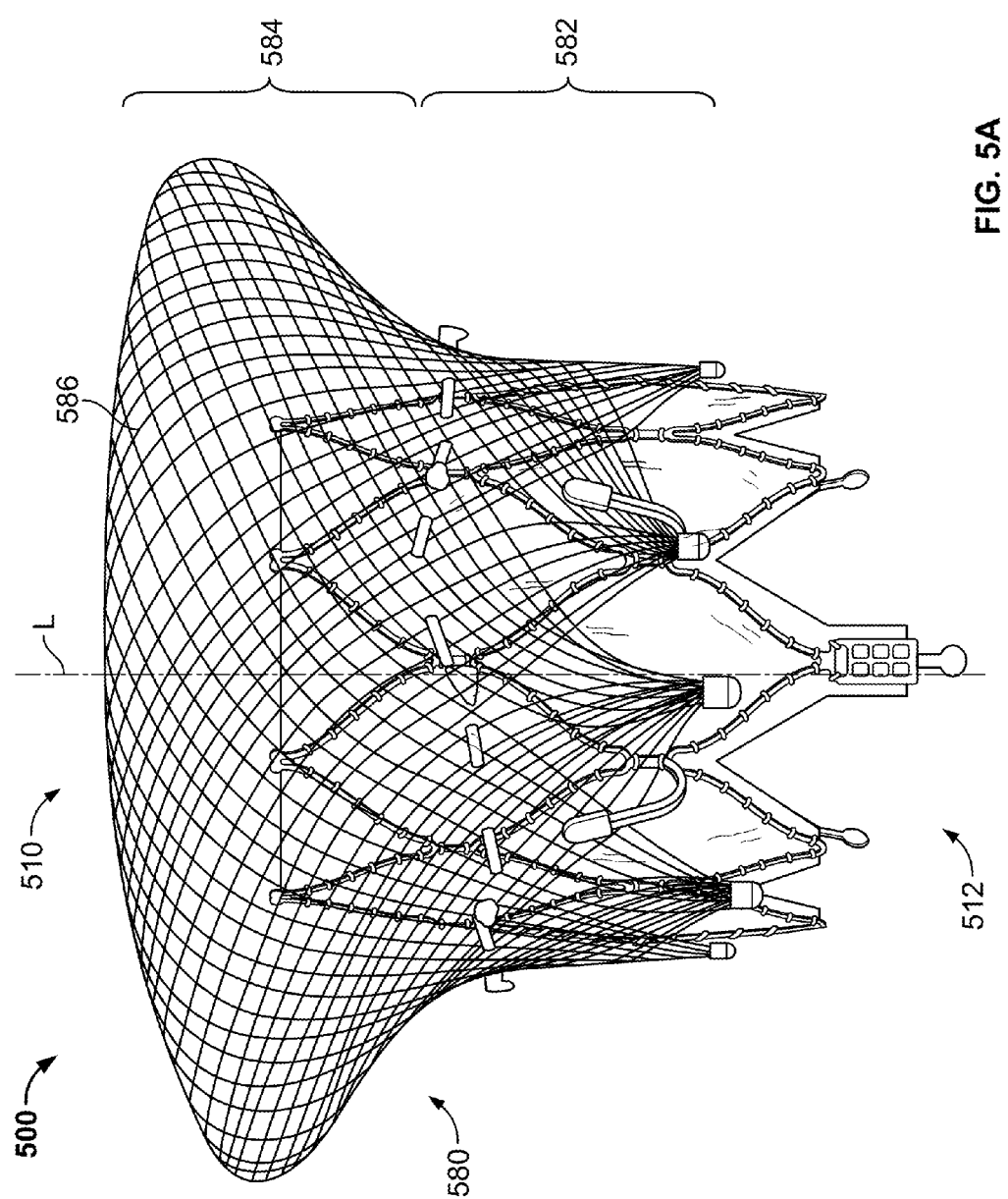

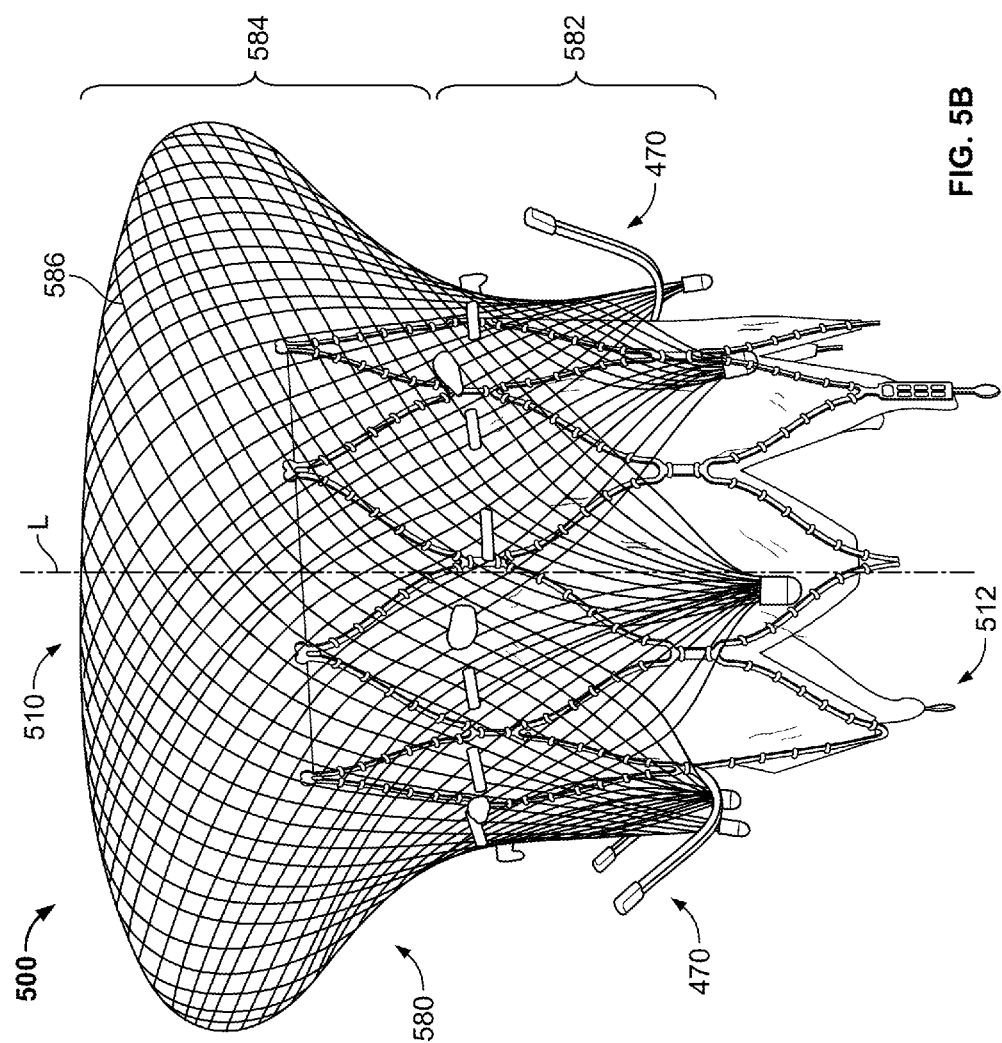

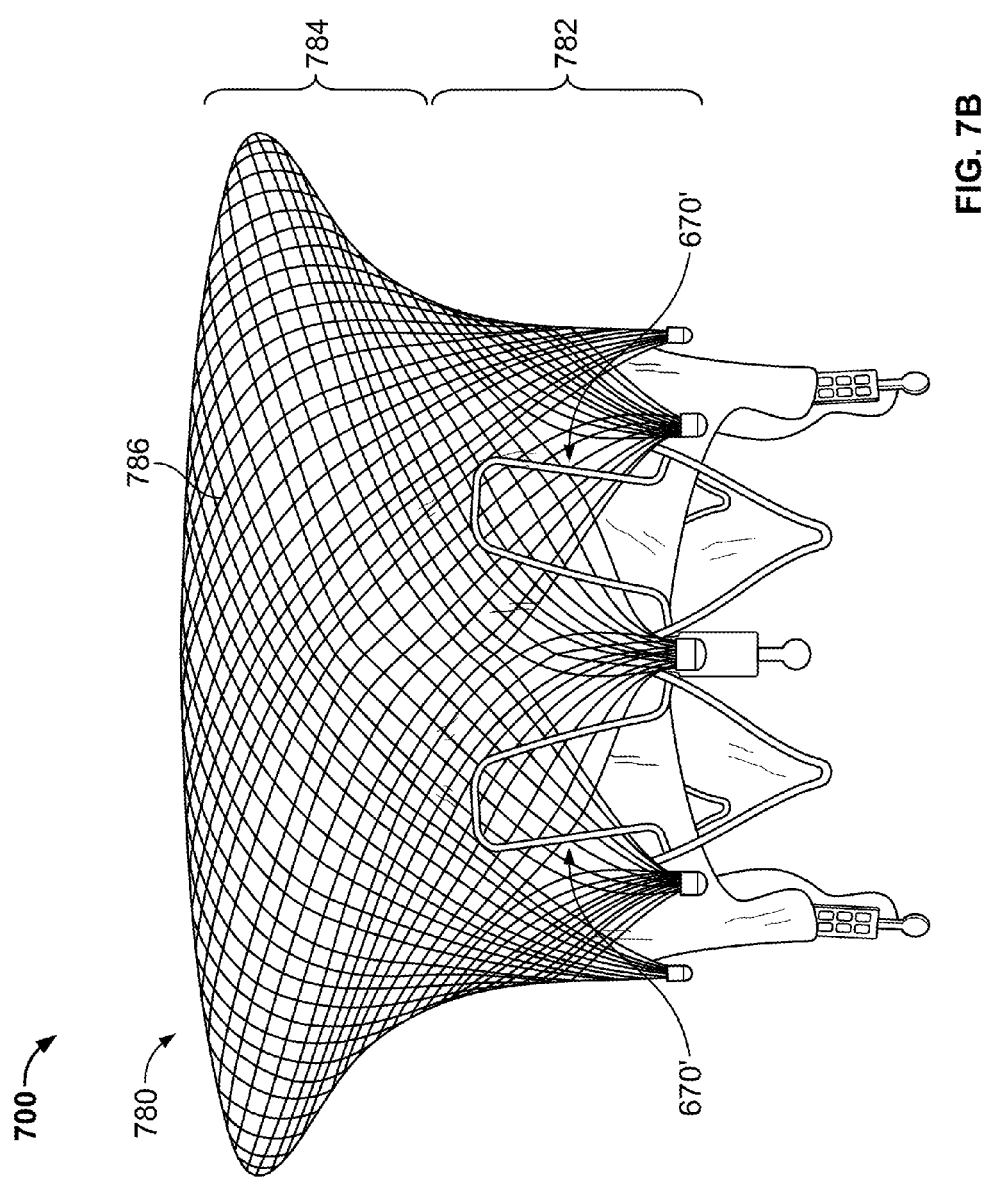

PROSTHETIC MITRAL VALVE

CROSS-REFERENCE TO RELATED APPLICATIONS

This application claims the benefit of the filing date of U.S. Provisional Patent Application No. 62/137,444 filed Mar. 24, 2015, the disclosure of which is hereby incorporated by reference herein.

BACKGROUND

The present disclosure relates to heart valve replacement and, in particular, to collapsible prosthetic heart valves. More particularly, the present disclosure relates to collapsible prosthetic heart valves having anchoring features.

Prosthetic heart valves that are collapsible to a relatively small circumferential size can be delivered into a patient less invasively than valves that are not collapsible. For example, a collapsible valve may be delivered into a patient via a tube-like delivery apparatus such as a catheter, a trocar, a laparoscopic instrument, or the like. This collapsibility can avoid the need for a more invasive procedure such as full open-chest, open-heart surgery.

Collapsible prosthetic heart valves typically take the form of a valve structure mounted on a stent. There are two types of stents on which the valve structures are ordinarily mounted: a self-expanding stent and a balloon-expandable stent. To place such valves into a delivery apparatus and ultimately into a patient, the valve is generally first collapsed or crimped to reduce its circumferential size.

When a collapsed prosthetic valve has reached the desired implant site in the patient (e.g., at or near the annulus of the patient's heart valve that is to be replaced by the prosthetic valve), the prosthetic valve can be deployed or released from the delivery apparatus and re-expanded to full operating size. For balloon-expandable valves, this generally involves releasing the entire valve, assuring its proper location, and then expanding a balloon positioned within the valve stent. For self-expanding valves, on the other hand, the stent automatically expands as the sheath covering the valve is withdrawn.

BRIEF SUMMARY

According to one aspect of the disclosure, a prosthetic heart valve has an inflow end and an outflow end. The prosthetic heart valve may include a stent having a collapsed condition, an expanded condition, and a plurality of cells arranged in circumferential rows. The prosthetic heart valve may also include an anchor arm having a body portion and a free end extending from the body portion. The body portion may be coupled to a perimeter of one of the plurality of cells, and the free end may extend toward the inflow end at a spaced distance radially outward from the body portion in an expanded condition of the anchor arm. The prosthetic heart valve may also include a valve assembly disposed within the stent and having a plurality of leaflets.

According to another aspect of the disclosure, a prosthetic heart valve includes an inflow end, an outflow end, and a stent having a collapsed condition, an expanded condition, and a plurality of cells arranged in circumferential rows. The prosthetic heart valve may also include an engaging arm pivotably disposed in one of the plurality of cells adjacent the outflow end, the engaging arm having a first strut coupled to the one cell, a second strut coupled to the one cell, and a third curved strut coupling the first strut to the second strut. The prosthetic heart valve may additionally include a flange formed of a braided mesh and having a body portion coupled to the stent and a flared portion adjacent the inflow end of the prosthetic heart valve. The prosthetic heart valve may further include a valve assembly disposed within the stent and having a plurality of leaflets.

BRIEF DESCRIPTION OF THE DRAWINGS

Various embodiments of the present disclosure are described herein with reference to the drawings, wherein:

FIG. 5A is a side view of a prosthetic heart valve according to a further aspect of the disclosure;

FIG. 5B is a side view of the prosthetic heart valve of FIG. 5A rotated about its longitudinal axis;

FIG. 7B is a side view of a prosthetic heart valve according to a further aspect of the disclosure incorporating features of the prosthetic heart valve of FIG. 7A;

DETAILED DESCRIPTION

Blood flows through the mitral valve from the left atrium to the left ventricle. As used herein, the term "inflow end," when used in connection with a prosthetic mitral heart valve, refers to the end of the heart valve closest to the left atrium when the heart valve is implanted in a patient, whereas the term "outflow end," when used in connection with a prosthetic mitral heart valve, refers to the end of the heart valve closest to the left ventricle when the heart valve is implanted in a patient. Also, as used herein, the terms "substantially," "generally," and "about" are intended to mean that slight deviations from absolute are included within the scope of the term so modified. Generally, materials described as being suitable for components in one embodiment may also be suitable for similar or identical components described in other embodiments.

Figure 1:
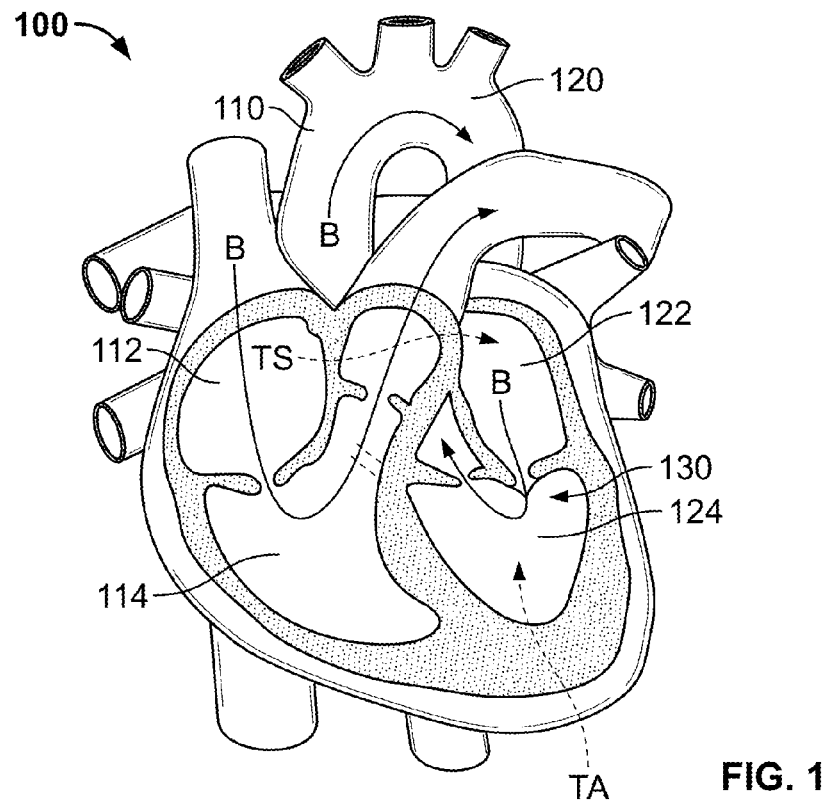
FIG. 1 is a highly schematic cutaway representation of a human heart showing various delivery approaches.

FIG. 1 is a highly schematic cutaway representation of human heart 100. The human heart includes two atria and two ventricles: right atrium 112 and left atrium 122, and right ventricle 114 and left ventricle 124. Heart 100 further includes aorta 110 and aortic arch 120. Disposed between left atrium 122 and left ventricle 124 is mitral valve 130. Mitral valve 130, also known as the bicuspid valve or left atrioventricular valve, is a dual-flap valve that opens as a result of increased pressure in left atrium 122 as it fills with blood. As atrial pressure increases above that of left ventricle 124, mitral valve 130 opens and blood passes into left ventricle 124. Blood flows through heart 100 in the direction shown by arrows "B".

A dashed arrow, labeled "TA", indicates a transapical approach of implanting a prosthetic heart valve, in this case to replace the mitral valve. In transapical delivery, a small incision is made between the ribs and into the apex of left ventricle 124 to deliver the prosthetic heart valve to the target site. A second dashed arrow, labeled "TS", indicates a transseptal approach of implanting a prosthetic heart valve in which the valve is passed through the septum between right atrium 112 and left atrium 122. Other approaches for implanting a prosthetic heart valve are also possible.

Figure 2:
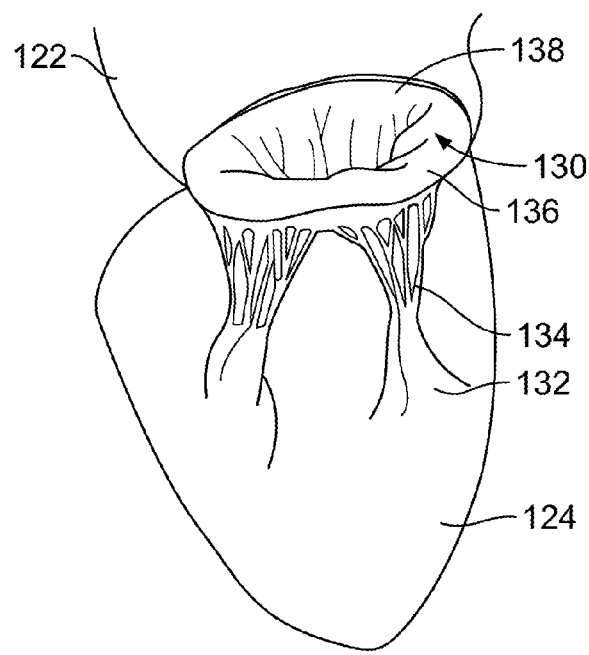
FIG. 2 is a highly schematic representation of a native mitral valve and associated cardiac structures.

FIG. 2 is a more detailed schematic representation of native mitral valve 130 and its associated structures. As previously noted, mitral valve 130 includes two flaps or leaflets, posterior leaflet 136 and anterior leaflet 138, disposed between left atrium 122 and left ventricle 124. Cord-like tendons, known as chordae tendineae 134, connect the two leaflets 136, 138 to the medial and lateral papillary muscles 132. During atrial systole, blood flows from higher pressure in left atrium 122 to lower pressure in left ventricle 124. When left ventricle 124 contracts in ventricular systole, the increased blood pressure in the chamber pushes leaflets 136, 138 to close, preventing the backflow of blood into left atrium 122. Since the blood pressure in left atrium 122 is much lower than that in left ventricle 124, leaflets 136, 138 attempt to evert to the low pressure regions. Chordae tendineae 134 prevent the eversion by becoming tense, thus pulling on leaflets 136, 138 and holding them in the closed position.

Figure 3A:
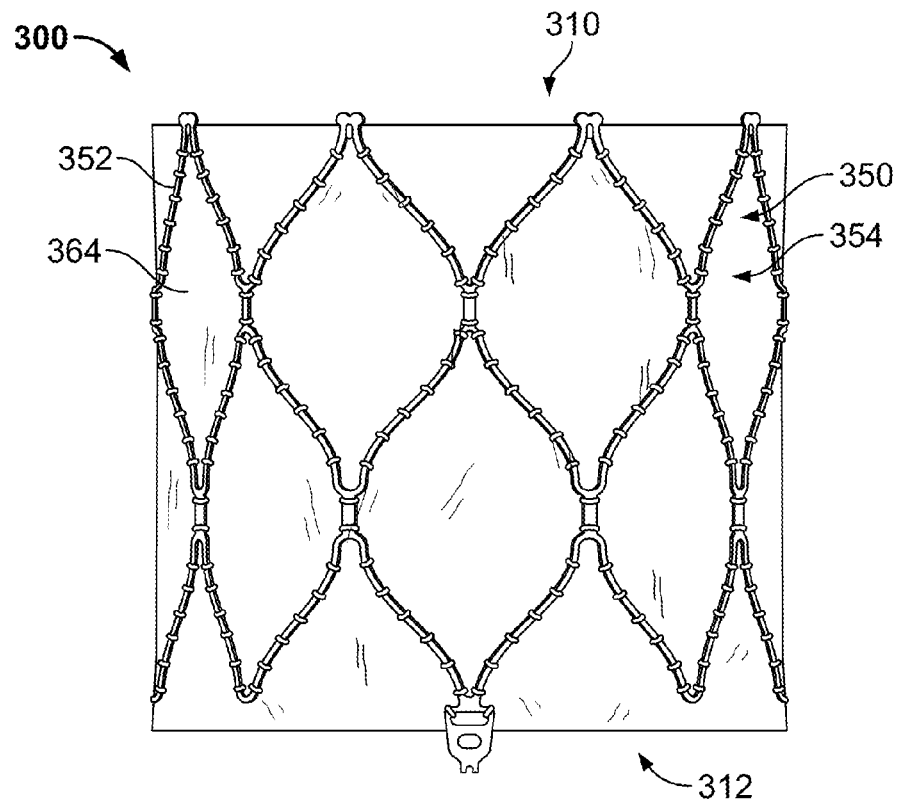
FIG. 3A is a side view of a prosthetic heart valve according to the prior art.
Figure 3B:
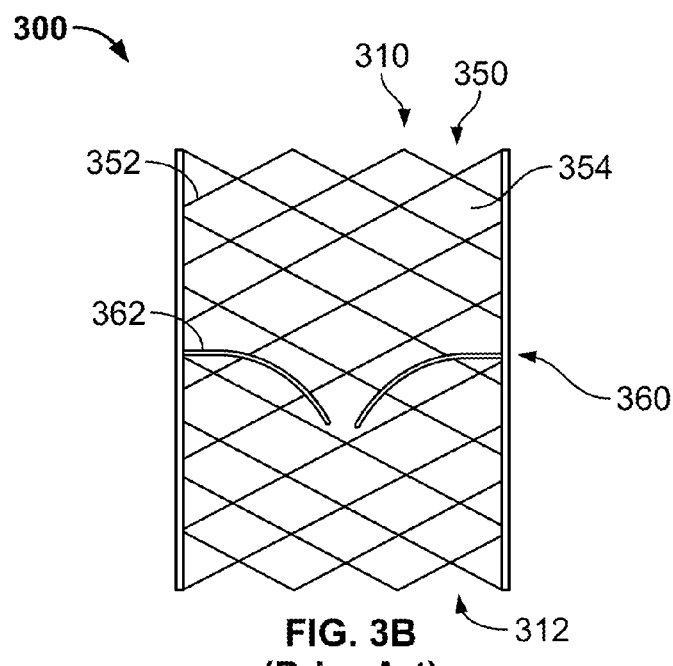
FIG. 3B is a highly schematic longitudinal cross-section of the prosthetic heart valve of FIG. 3A.

FIGS. 3A and 3B are a side view and a longitudinal cross-sectional view of prosthetic heart valve 300 according to the prior art. Prosthetic heart valve 300 is a collapsible prosthetic heart valve designed to replace the function of the native mitral valve of a patient (see native mitral valve 130 of FIGS. 1-2). Generally, prosthetic valve 300 has a substantially cylindrical shape with inflow end 310 and outflow end 312. When used to replace native mitral valve 130, prosthetic valve 300 may have a low profile so as not to interfere with atrial function in the native valve annulus.

Prosthetic heart valve 300 may include stent 350, which may be formed from biocompatible materials that are capable of self-expansion, such as, for example, shape-memory alloys including Nitinol. Stent 350 may include a plurality of struts 352 that form cells 354 connected to one another in one or more annular rows around the stent. Cells 354 may all be of substantially the same size around the perimeter and along the length of stent 350. Alternatively, cells 354 near inflow end 310 may be larger than the cells near outflow end 312. Stent 350 may be expandable to provide a radial force to assist with positioning and stabilizing prosthetic heart valve 300 in the native valve annulus.

Prosthetic heart valve 300 may also include a substantially cylindrical valve assembly 360 including a plurality of leaflets 362 (FIG. 3B) attached to a cuff 364 (FIG. 3A). Leaflets 362 replace the function of native mitral valve leaflets 136 and 138 described above with reference to FIG. 2. That is, leaflets 362 coapt with one another to function as a one-way valve. The valve assembly 360 of prosthetic heart valve 300 may include two or three leaflets, but it should be appreciated that prosthetic heart valve 300 may have more than three leaflets. Both cuff 364 and leaflets 362 may be wholly or partly formed of any suitable biological material, such as bovine or porcine pericardium, or polymers, such as polytetrafluoroethylene (PTFE), urethanes and the like. Valve assembly 360 may be secured to stent 350 by suturing to struts 352 or by using tissue glue, ultrasonic welding or other suitable methods.

When prosthetic heart valve 300 is implanted in a patient, for example at the annulus of native mitral valve 130, it is biased towards an expanded condition, providing radial force to anchor the valve in place. However, if the radial force is too high, damage may occur to heart tissue. If, instead, the radial force is too low, the heart valve may move from its implanted position, for example, into either left ventricle 124 or left atrium 122, requiring emergency surgery to remove the displaced valve. The potential for such movement may be heightened in mitral valve applications, particularly if a low profile valve is used.

Another potential issue with prosthetic heart valves is inadequate sealing between the prosthetic valve and the native tissue. For example, if prosthetic heart valve 300 is implanted at the annulus of mitral valve 130 in a patient, improper or inadequate sealing may result in blood flowing from left ventricle 124 into left atrium 122, even if leaflets 362 of valve assembly 360 are working properly. This may occur, for example, if blood flows in a retrograde fashion between the outer perimeter of prosthetic heart valve 300 and the native tissue at the site of implantation. This phenomenon is known as perivalvular (or paravalvular) leak ("PV leak").

Figure 4A:
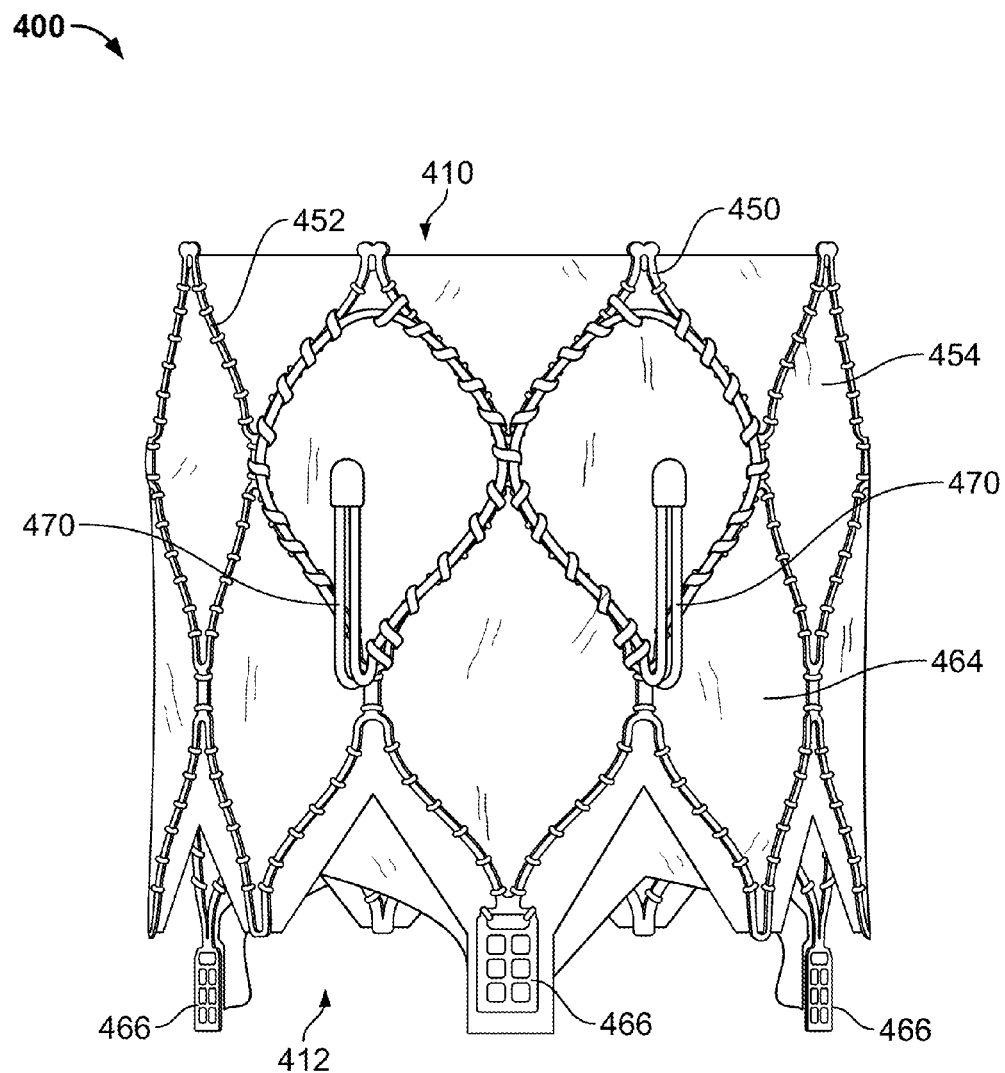
FIG. 4A is a side view of a prosthetic heart valve according to an aspect of the disclosure.
Figure 4B:
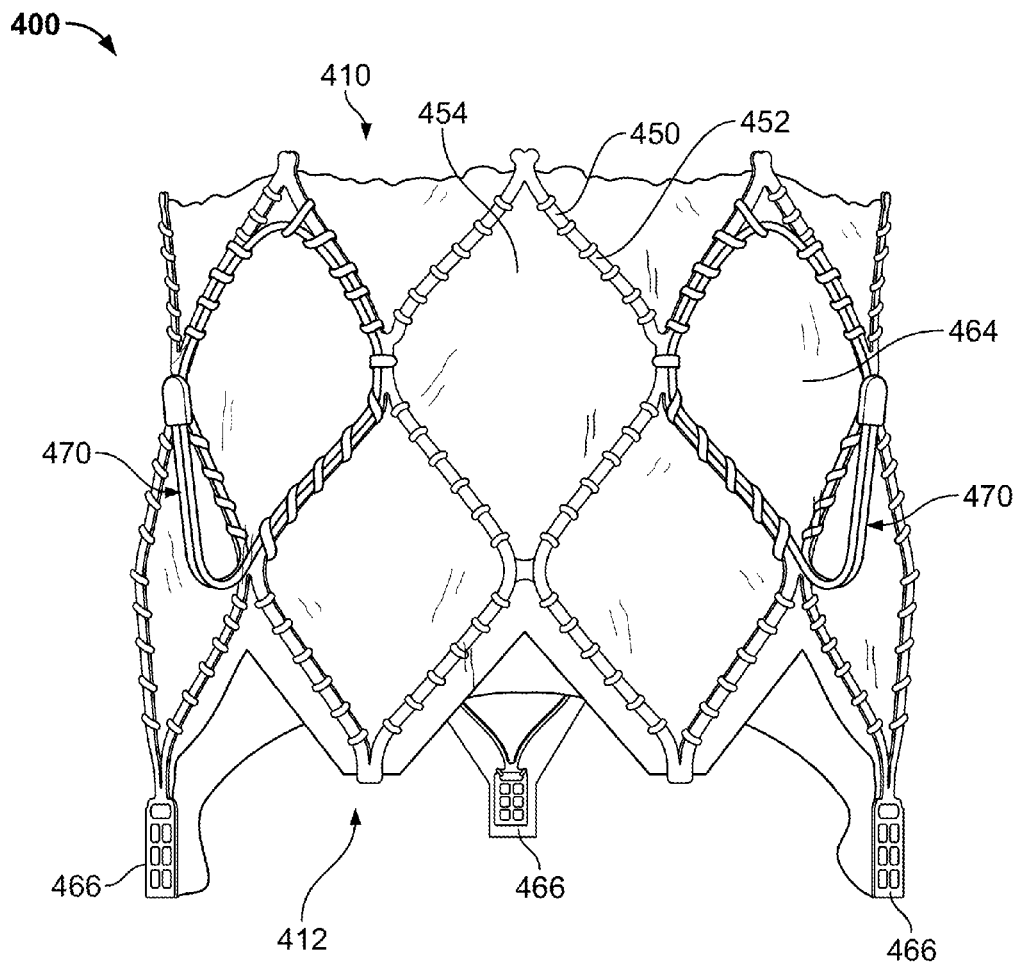
FIG. 4B is a side view of the prosthetic heart valve of FIG. 4A rotated about its longitudinal axis.
Figure 4C:
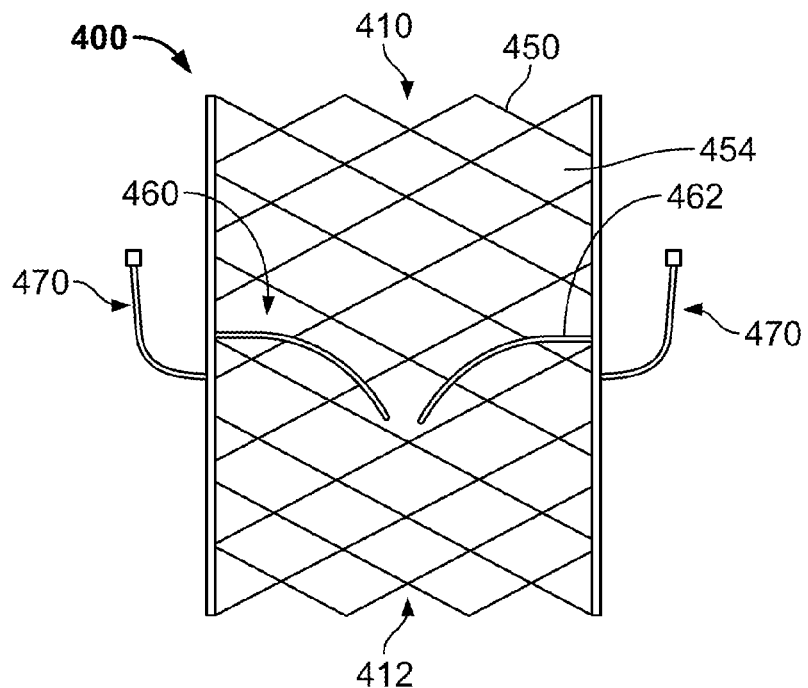
FIG. 4C is a highly schematic longitudinal cross-section of the prosthetic heart valve of FIG. 4A.

FIG. 4A is a side view of a prosthetic heart valve 400 in accordance with one embodiment of the disclosure. FIG. 4B shows prosthetic heart valve 400 rotated approximately 180 degrees about its longitudinal axis compared to FIG. 4A. Prosthetic heart valve 400 may be similar or identical to prosthetic heart valve 300 in certain respects. For example, prosthetic heart valve 400 is collapsible and expandable and designed for replacement of a native mitral valve, having a substantially cylindrical shape with an inflow end 410 and an outflow end 412. It should be understood that prosthetic heart valve 400 is not limited to replacement of mitral valves, and may be used to replace other heart valves. Prosthetic heart valve 400 may include stent 450, which may be similar to stent 350, having a plurality of struts 452 that form cells 454 connected to one another in one or more annular rows around stent 450. Stent 450 includes two annular rows of cells 454 of substantially similar size and shape, with nine cells in each row. As illustrated, cells 454 are generally diamond shaped. However, it should be understood that a different number of rows of cells 454, as well as a different number of cells 454 per row, may be suitable. Also, as discussed in relation to stent 350, stent 450 may be formed from a shape memory alloy, such as Nitinol. The struts 452 forming stent 450 may have a diameter of between about 0.020 inches (0.51 mm) and about 0.025 inches (0.64 mm), although other dimensions may be suitable. Forming stent 450 from struts 452 of a relatively large diameter may provide increased stiffness to stent 450, which may provide certain benefits, such as minimizing the deflection of commissure attachment features (CAFs) 466 during normal operation of prosthetic heart valve 400. On the other hand, forming stent 450 from struts 452 of a relatively small diameter may provide increased flexibility to stent 450, which may provide certain benefits, such as the capability to be collapsed to a smaller profile during delivery.

Prosthetic heart valve 400 may also include valve assembly 460 having three leaflets 462 attached to a cylindrical cuff 464. It should be understood that although native mitral valve 130 has two leaflets 136, 138, prosthetic heart valve 400 may have three leaflets, or more or fewer than three leaflets, provided that the leaflets act to allow one-way antegrade blood flow through the prosthetic heart valve 400. Because prosthetic heart valve 400 has three leaflets 462, it also has three CAFs 466, which provide points of attachment for adjacent leaflets 462 to stent 450. It should be understood that prosthetic heart valve 400 may alternatively include a pair of prosthetic leaflets and a corresponding pair of CAFs.

As with stent 350, stent 450 may be expandable to provide a radial force to assist with positioning and stabilizing prosthetic heart valve 400 in the native mitral valve annulus. However, prosthetic valve 400 includes additional securement features in the form of anchor arms 470 that hook under native mitral valve leaflets 136, 138 to help prevent prosthetic heart valve 400 from migrating into left atrium 122.

Figure 4D:
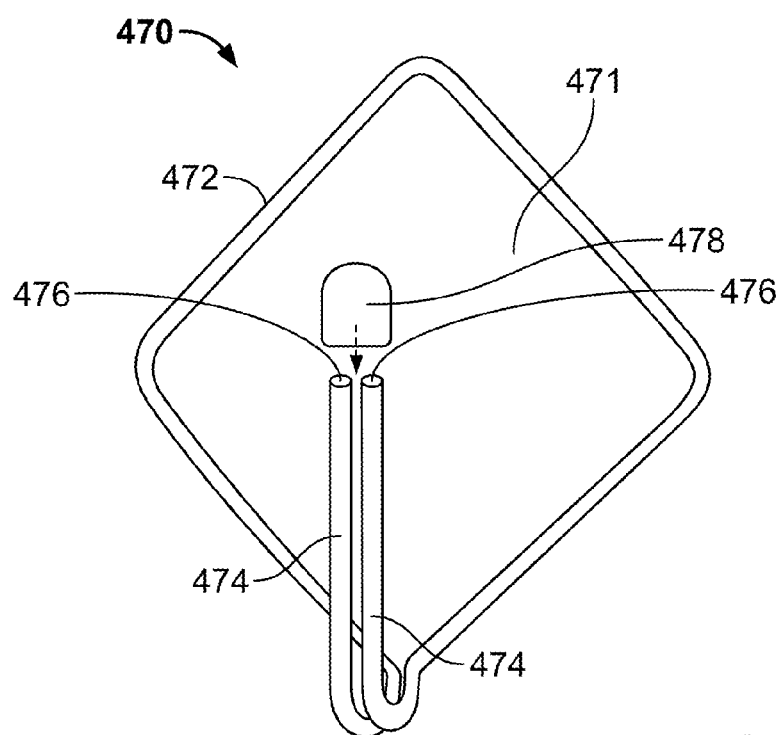
FIG. 4D is an isolated perspective view of an anchor feature of the prosthetic heart valve of FIG. 4A.

A single anchor arm 470 is shown in FIG. 4D. Anchor arm 470 may be formed of a single wire 472 bent or otherwise formed into a body portion 471 having a substantially diamond shape. Wire 472 is preferably a shape-memory alloy such as Nitinol. In one example, wire 472 is formed of Nitinol having a diameter of about 0.015 inches (0.38 mm). As with struts 452 of stent 450, the diameter of wire 472 may be increased to provide increased stiffness or decreased to provide increased flexibility. Although the shape of body portion 471 may vary, it preferably corresponds to the geometry of a single cell 454 of stent 450. Wire 472 has two free end portions 474 that extend adjacent and substantially parallel to one another, and that are curved or hooked so as to lie at a spaced distance radially outward from body portion 471. Preferably, the tip 476 of each free end portion 474 is blunt and/or rounded to reduce the likelihood of tips 476 damaging the native tissue hooked by anchor arm 470. In addition or alternatively, a blunted and/or rounded end cap 478 may be assembled over or onto the tips 476 of free end portions 474 and fixed to tips 476, for example by welding, to provide an atraumatic tissue contact surface.

Figure 4E:
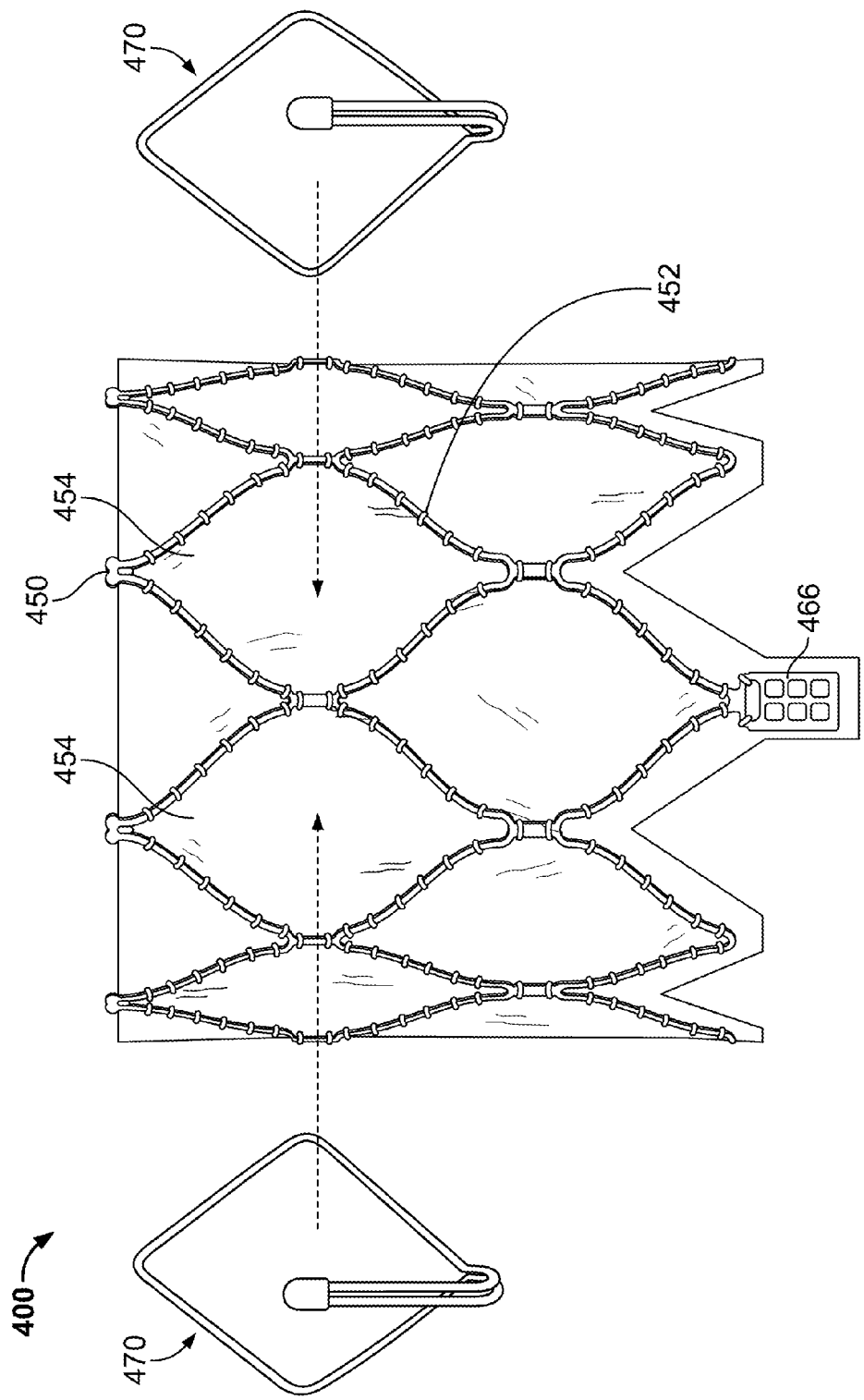
FIG. 4E is a side view of the prosthetic heart valve of FIG. 4A in a stage of manufacture.

Prosthetic heart valve 400 is shown at a stage of manufacture in FIG. 4E to better illustrate the attachment of anchor arms 470 to prosthetic heart valve 400. After valve assembly 460 and cuff 464 have been attached to stent 450, anchor arms 470 may be coupled to prosthetic heart valve 400 at desired locations around stent 450. As shown in FIG. 4E, anchor arms 470 may be positioned within and/or adjacent to a selected cell 454 of stent 450 and connected to the prosthetic heart valve 400, for example by suturing body portion 471 of anchor arm 470 to the struts 452 defining the perimeter of selected cell 454. The sutures coupling anchor arms 470 to prosthetic heart valve 400 may additionally pass through cuff 464. Forces applied to free end portions 474 are transmitted to the body portion 471 of anchor arm 470. With the above-described configuration of anchor arm 470 and its attachment to cell 454, those transmitted forces are distributed over a larger area of stent 450, providing better reinforcement than if free end portions 474 were sewn or otherwise directly connected to stent 450 without the use of body portion 471.

Figure 4F:
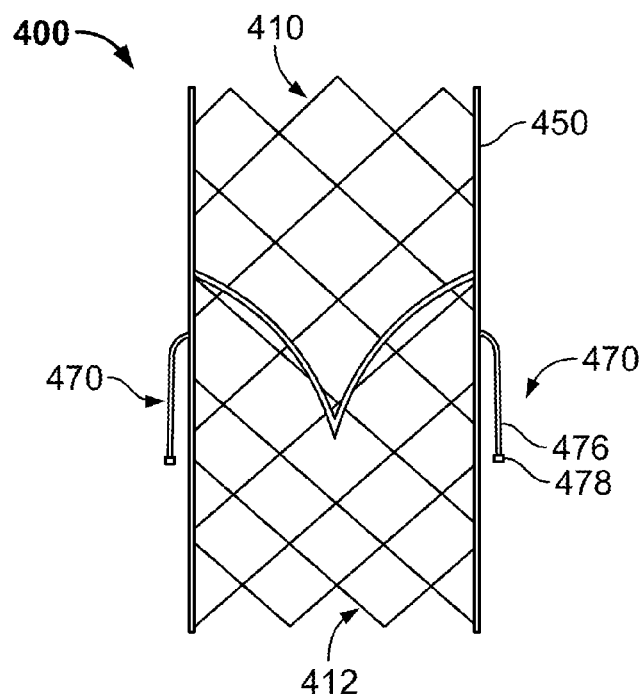
FIG. 4F is a highly schematic longitudinal cross-section of the prosthetic heart valve of FIG. 4A in a collapsed condition.
Figure 4G:
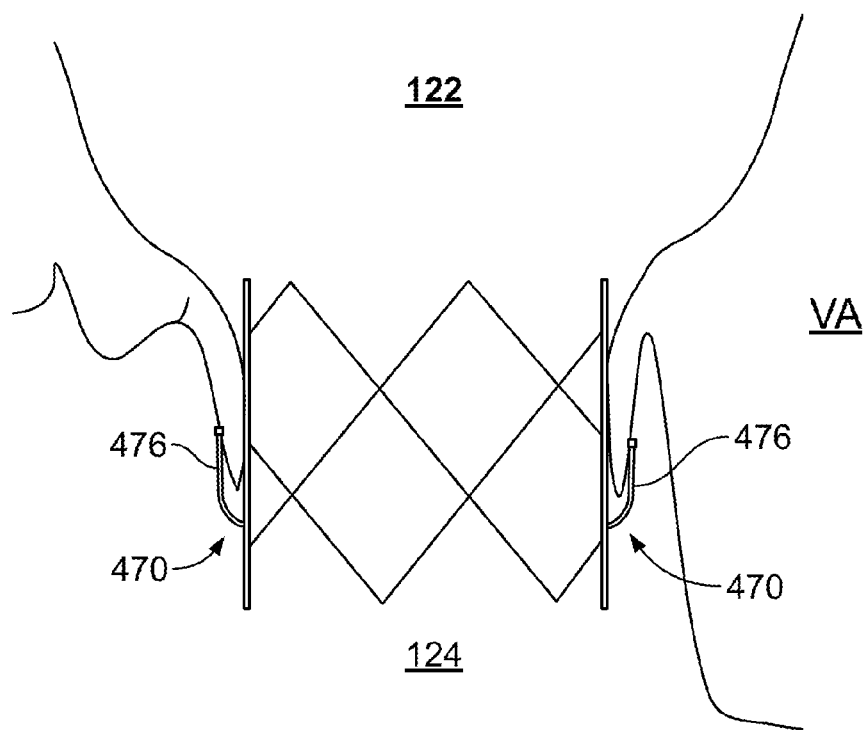
FIG. 4G is a highly schematic representation of the prosthetic heart valve of FIG. 4A implanted into a native mitral valve annulus.

As noted above, wire 472 forming anchor arms 470 is preferably made from a shape-memory alloy. By using a shape-memory alloy, the shape of anchor arms 470 may be set, for example by heat setting, to take the illustrated shape in the absence of applied forces. However, forces may be applied to anchor arms 470 and to prosthetic heart valve 400 generally to reduce radial size and/or bulk of the prosthetic heart valve when in the collapsed condition, which may facilitate intravascular (or other minimally invasive) delivery of the prosthetic heart valve via a delivery device (not shown). For example, as shown in FIG. 4F, prosthetic heart valve 400 may be transitioned to the collapsed condition, with free end portions 474 of anchor arms 470 being distorted or "flipped" to point toward outflow end 412 rather than inflow end 410. Prosthetic heart valve 400 may be maintained in the collapsed condition, for example by a surrounding sheath of a delivery device (not shown), as prosthetic heart valve 400 is delivered to native mitral valve 130. When in a desired position relative to native mitral valve 130, prosthetic heart valve 400 may be released from the delivery device. As constraining forces are removed from prosthetic heart valve 400, it begins to transition to the expanded condition, while anchor arms 470 move to their preset shape. Since anchor arms 470 are shape-set so that their free end portions 474 point toward inflow end 410, anchor arms 470 revert to that shape when released from the delivery device. As the free end portions 474 of anchor arms 470 transition from pointing toward outflow end 412 to pointing toward inflow end 412, native mitral valve leaflets 136, 138 are captured between the free end portions 474 and the body of stent 450, as shown in FIG. 4G. When hooked around native mitral valve leaflets 136, 138, anchor arms 470 help anchor prosthetic heart valve 400 within native valve annulus VA and are particularly effective at resisting migration of the prosthetic heart valve into left atrium 122. Distorting or flipping the anchor arms 470 while prosthetic heart valve 400 is maintained in the collapsed condition may reduce the profile of the collapsed valve, although prosthetic heart valve 400 may alternatively be put in the collapsed condition without distorting or flipping anchor arms 470.

Figure 4H:
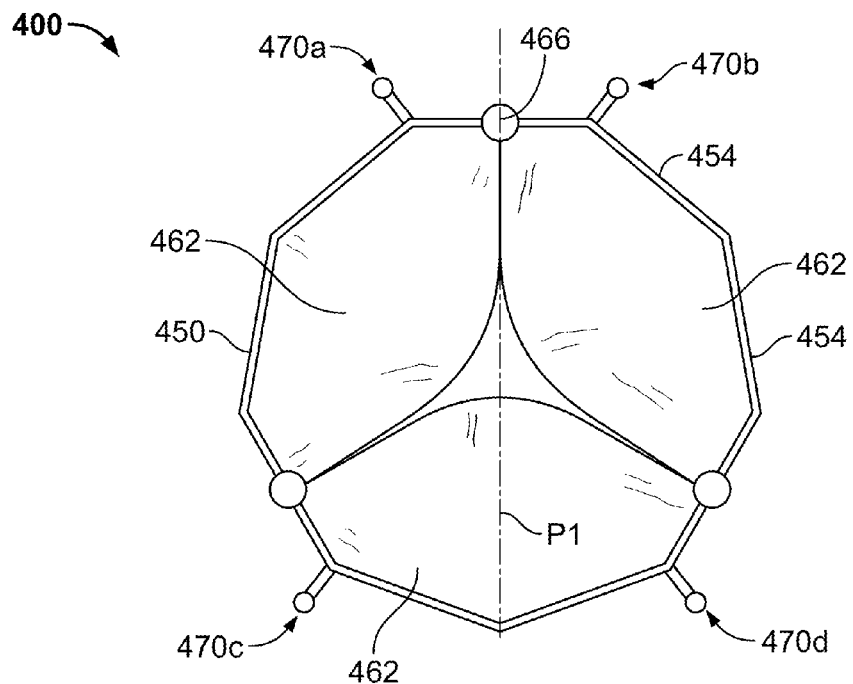
FIG. 4H is a highly schematic bottom view of the outflow end of the prosthetic heart valve of FIG. 4A.

As described above, the stent 450 of prosthetic heart valve 400 may include two circumferential rows of annular cells 454, with each row containing nine cells 454. Although the use of nine cells 454 is merely an example, the use of an odd number of cells 454 in prosthetic heart valves for replacing native mitral valve 130 may cause difficulty in creating symmetry in the positioning of anchor arms 470 on the prosthetic heart valve. For example, it is preferable, although not necessary, to use two anchor arms 470 for each of the two native mitral valve leaflets to better distribute the forces caused by hooking or clamping native the mitral valve leaflets between anchor arms 470 and stent 450. With nine substantially equally-sized cells 454, or any other odd number of similarly sized cells 454, symmetry in the positioning of anchor arms 470 is difficult to achieve. FIG. 4H shows prosthetic heart valve 400 as viewed from outflow end 412. It should be understood that although stent 450 is illustrated as a regular nine-sided polygon (with each side representing a single cell 454), this representation is for purposes of clarity only and prosthetic heart valve 400, including stent 450, may take a substantially cylindrical shape when in the expanded condition. As shown in FIG. 4H, two anchor arms 470a and 470b may be coupled to stent 450 at adjacent cells 454, for example on cells 454 on either side of a CAF 466. The remaining two anchor arms 470c and 470d cannot be placed on adjacent cells 454 diametrically opposed to anchor arms 470a and 470b so as to maintain the symmetry of anchor arms 470. When positioning two pairs of anchor arms on substantially diametrically opposed portions of stent 450, it is preferable to maintain the symmetry of the anchor arms relative to at least one plane P1 dividing prosthetic heart valve 400. As shown in FIG. 4H, for a stent having nine substantially similarly-sized cells, this symmetry may be achieved by coupling the other pair of anchor arms 470c and 470d to stent 450 at two cells 454 that are separated by one cell 454. When implanting prosthetic heart valve 400, it is preferable to hook anchor arms 470a and 470b under posterior leaflet 136 of native mitral valve 130, with anchor arms 470c and 470d hooked under anterior leaflet 138 of native mitral valve 130. With this configuration, one CAF 466 abuts posterior leaflet 136 and two CAFs abut anterior leaflet 138.

Figure 4I:
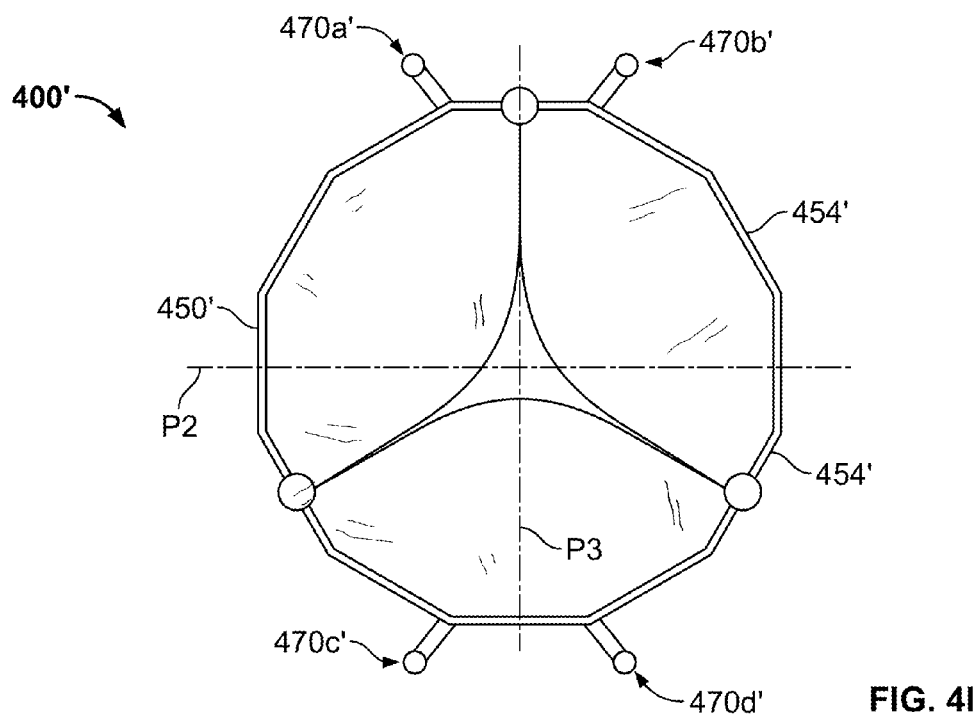
FIG. 4I is a highly schematic bottom view of the outflow end of a prosthetic heart valve according to another aspect of the disclosure.

The teachings provided above in connection with prosthetic heart valve 400 may be applied to a stent 450' that is similar to stent 450, but that has an even number of cells 454'. For example, FIG. 4I shows a prosthetic heart valve 400' that incorporates a stent 450' having two circumferential rows of twelve cells 454' having substantially equal sizes. Similar to the illustration of FIG. 4H, stent 450' in FIG. 4I is shown as a regular twelve-sided polygon for purposes of clarity only, and prosthetic heart valve 400' and stent 450' may be substantially cylindrical when in the expanded condition. The use of a stent 450' having an even number of substantially similarly sized cells 454' makes it easier to couple a first pair of anchor arms 470a' and 470b' to a first side of stent 450' and a second pair of anchor arms 470c' and 470d' to a diametrically-opposed second side of stent 450' while maintaining the symmetry of the anchor arms 470a'-470d' relative to two planes P2, P3. In other words, the circumferential spacing between anchor arms 470a' and 470b' may be substantially equal to the spacing between anchor arms 470c' and 470d', while the circumferential spacing between anchor arms 470a' and 470c' may be substantially equal to the spacing between anchor arms 470b' and 470d'. When prosthetic heart valve 400' is implanted, this symmetry about two planes P2, P3 may provide for a more uniform distribution of forces than prosthetic heart valves exhibiting such symmetry in less than two planes (such as prosthetic heart valve 400 described above). In addition, the twelve-cell configuration may provide for more uniform expansion of the stent compared to the nine-cell configuration.

While prosthetic heart valve 400 may be used as shown and described above in connection with FIGS. 4A-I, a prosthetic heart valve may be provided with additional anchoring and/or sealing elements. For example, FIGS. 5A-D illustrate a prosthetic heart valve 500 that essentially comprises prosthetic heart valve 400 with a flange 580 coupled thereto. Flange 580 may facilitate the anchoring of heart valve 500 within native mitral valve annulus 130 and the prevention of PV leak. Flange 580 may be formed of a material braided to create various shapes and/or geometries to engage tissue. As shown in FIGS. 5A-D, flange 580 includes a plurality of braided strands or wires 586 arranged in three dimensional shapes. In one example, wires 586 form a braided metal fabric that is resilient, collapsible and capable of heat treatment to substantially set a desired shape. One class of materials which meets these qualifications is shape-memory alloys, such as Nitinol. Wires 586 may comprise various materials other than Nitinol that have elastic and/or memory properties, such as spring stainless steel, tradenamed alloys such as Elgiloy® and Hastelloy®, CoCrNi alloys (e.g., tradename Phynox), MP35N®, CoCrMo alloys, or a mixture of metal and polymer fibers. Depending on the individual material selected, the strand diameter, number of strands, and pitch may be altered to achieve the desired shape and properties of flange 580.

Figure 5C:
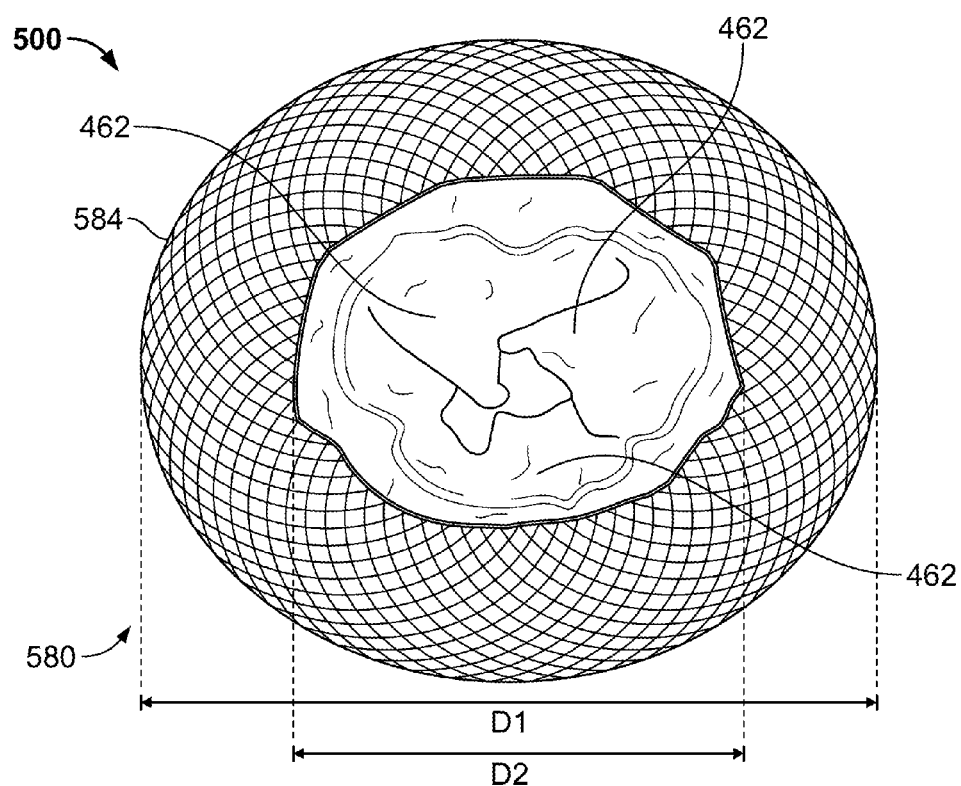
FIG. 5C is a top view of the inflow end of the prosthetic heart valve of FIG. 5A.
Figure 5D:
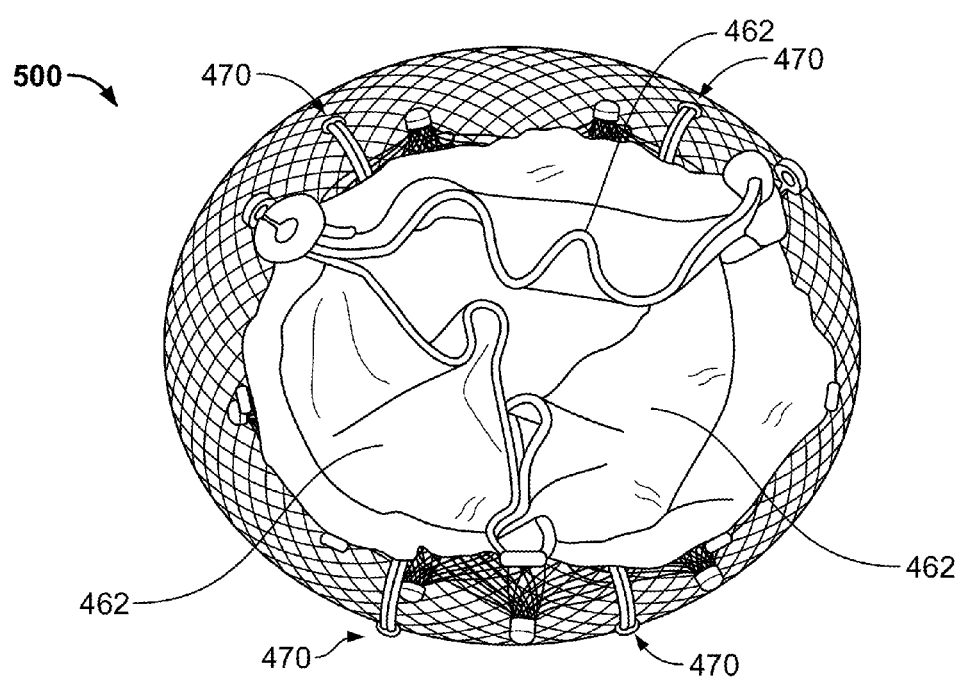
FIG. 5D is a bottom view of the outflow end of the prosthetic heart valve of FIG. 5A.
Figure 5E:
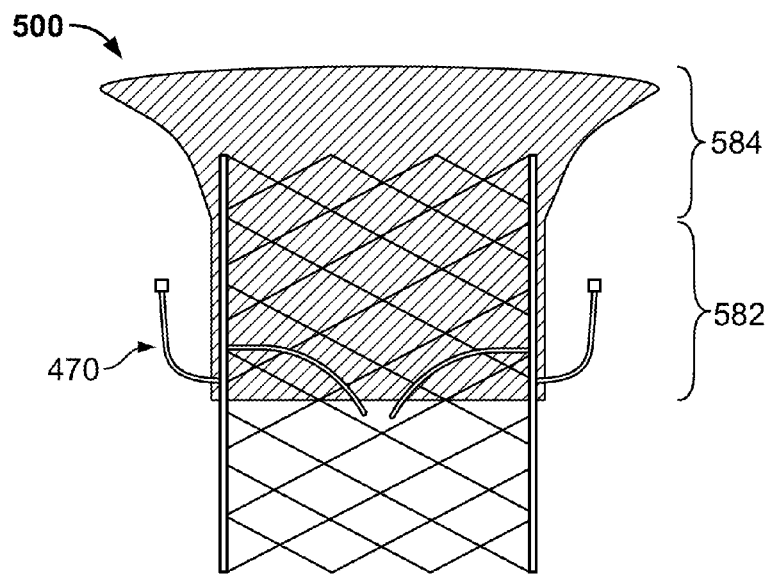
FIG. 5E is a highly schematic longitudinal cross-section of the prosthetic heart valve of FIG. 5A in the expanded condition.

Flange 580 may include a body portion 582 terminating at an outflow end of the flange and a flared portion 584 terminating at an inflow end of the flange. Body portion 582 may be formed with a cylindrical or tubular geometry and may be configured to be circumferentially disposed around a portion of stent 450 and/or valve assembly 460. Flange 580 may be coupled to stent 450 (and optionally to valve assembly 460 and/or cuff 464) by sutures, for example. Flange 580 may be alternatively or additionally connected to stent 450 via ultrasonic welds, glue, adhesives, or other suitable means. When coupled to stent 450, body portion 582 of flange 580 is nearer outflow end 512 and flared portion 584 is nearer inflow end 510. When in the expanded condition, flared portion 584 extends a greater distance radially outwardly from the longitudinal axis L of prosthetic heart valve 500 than body portion 582. In other words, as shown in FIG. 5C, flared portion 584 may have a diameter D1 that is greater than the diameter D2 of body portion 582 when prosthetic heart valve 500 is in the expanded condition. In addition, the distance which flared portion 584 extends radially outwardly from longitudinal axis L may increase nearer inflow end 510.

Figure 5F:
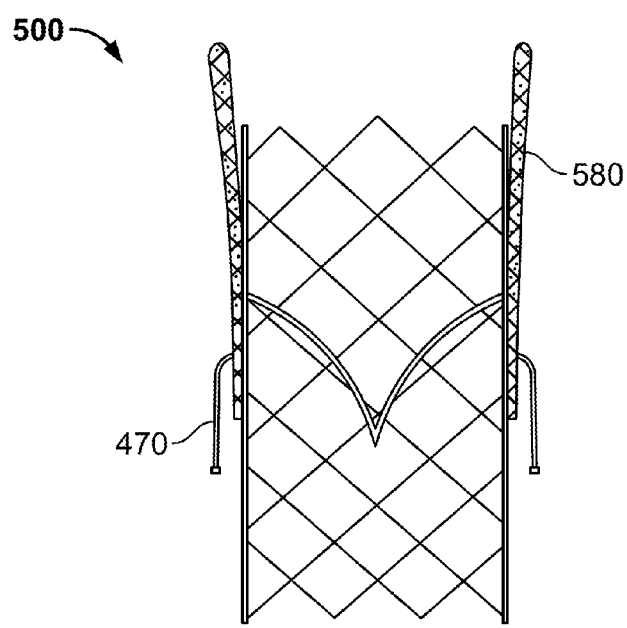
FIG. 5F is a highly schematic longitudinal cross-section of the prosthetic heart valve of FIG. 5A in the collapsed condition.
Figure 5G:
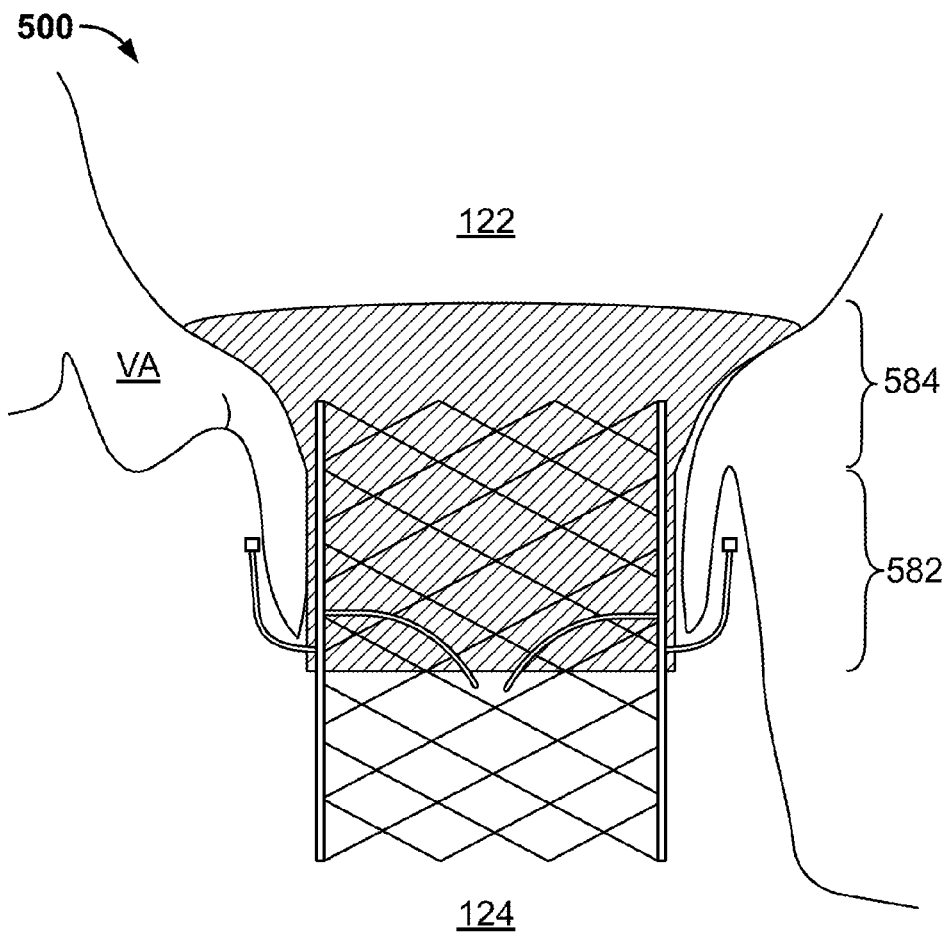
FIG. 5G is a highly schematic representation of the prosthetic heart valve of FIG. 5A implanted into a native mitral valve annulus.

Flange 580 may be preset to take the illustrated trumpet shape in the absence of external forces. As with stent 450 and anchor arms 470, flange 580 may be collapsed to a decreased profile to facilitate minimally invasive delivery. For example, prosthetic heart valve 500 may be transitioned from the expanded condition (FIGS. 5A-E) to the collapsed condition (FIG. 5F) and maintained in the collapsed condition by a surrounding sheath of a delivery device. Anchors 470 may flip and point toward outflow end 512 as described in connection with FIG. 4F, and flange 580 may collapse radially inwardly and become substantially cylindrical and/or significantly less flared than in the expanded condition. Body 582 of flange 580 may be positioned between anchor arms 470 and the remainder of stent 450. Prosthetic heart valve 500 may be delivered to the implant site in the collapsed condition and, when in the desired position relative to native mitral valve 130, transitioned to the expanded condition, for example by removing the surrounding sheath of the delivery device. During the transition from the collapsed condition to the expanded condition, anchor arms 470 revert to the preset shape as described in connection with FIG. 4F, capturing native mitral valve leaflets 136, 138 between anchor arms 470 and corresponding portions of stent 450. Flange 580 also transitions from the collapsed condition to the expanded condition, assuming its preset shape shown in FIG. 5G. When implanted and in the expanded condition, flange 580 provides a large surface area to help anchor prosthetic valve 500 within native valve annulus VA, and may be particularly effective at resisting movement of prosthetic heart valve 500 toward left ventricle 124. Specifically, flange 580 has an expanded diameter that is too large to pass through native valve annulus VA. Because flange 580 is coupled to stent 450, prosthetic heart valve 500 is restricted from migrating into left ventricle 124 during normal operation of prosthetic heart valve 500. Thus, the combination of anchor arms 470 engaged with the mitral valve leaflets, and flange 580 engaged with the tissue on the atrial side of the mitral valve annulus, helps to securely anchor prosthetic heart valve 500 within the mitral valve annulus and limits its migration toward either the left atrium or the left ventricle.

Figure 5H:
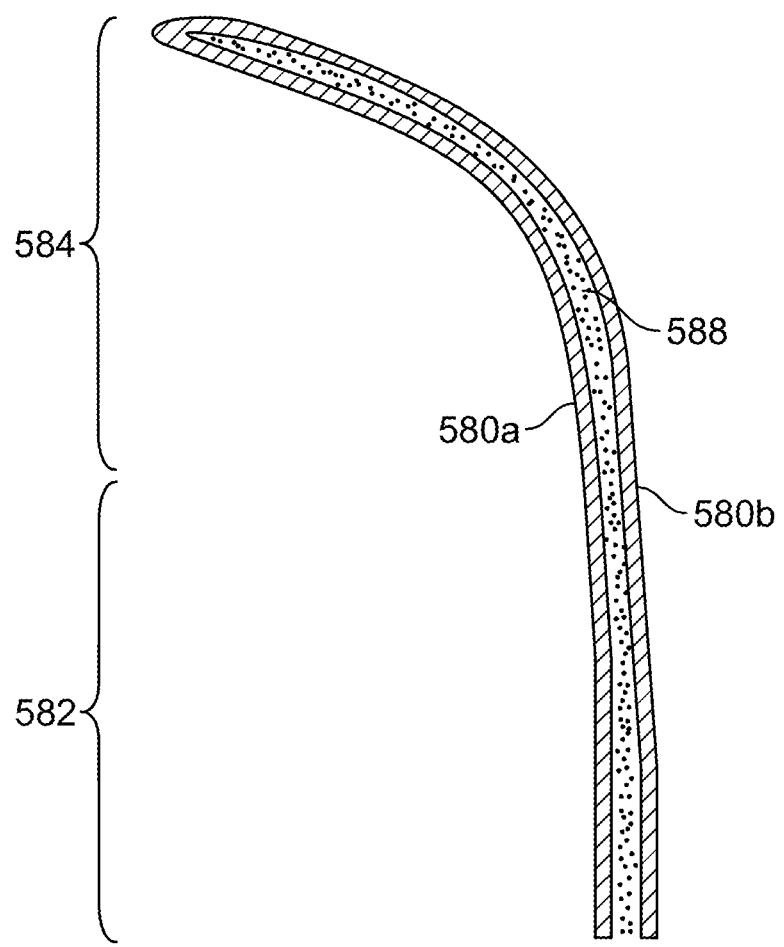
FIG. 5H is a highly schematic cross-section of a portion of the flange of the prosthetic heart valve of FIG. 5A.

In addition to providing anchoring capabilities, flange 580 may improve sealing between prosthetic heart valve 500 and native valve annulus VA. In particular, as shown in FIG. 5H, flange 580 may be formed with an outer layer 580a and an inner layer 580b, for example by folding one portion of braided wires 586 over another portion of braided wires 586. A fabric layer 588, such as a polyester fabric, may be inserted or sandwiched between outer layer 580a and inner layer 580b. Fabric layer 588 may enhance tissue ingrowth into prosthetic heart valve 500 after implantation and may also enhance the fluid seal, and thus help prevent PV leak, between the outer diameter of prosthetic heart valve 500 and the adjacent portions of native mitral valve annulus VA. Although flange 580 is described as being folded over onto itself, alternative configurations may be suitable for holding fabric layer 588, for example by weaving or braiding two separate layers of braided wires 586 together. In a variation hereof, a single fabric layer 588 may be applied to the outside surface of flange 580, to the inside surface of flange 580, or to both the outside and inside surfaces of flange 580 to improve sealing between prosthetic heart valve 500 and native valve annulus VA.

Figure 6A:
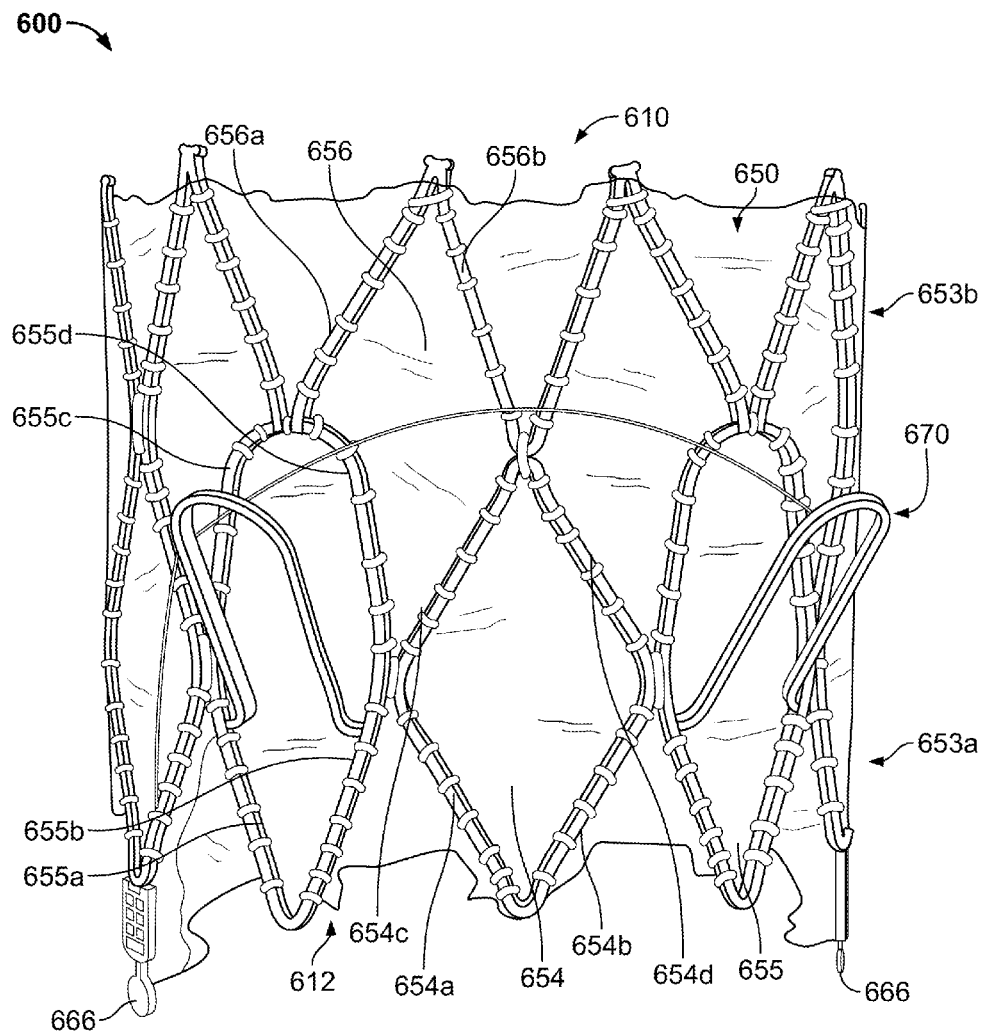
FIG. 6A is a side view of a prosthetic heart valve according to yet another aspect of the disclosure.
Figure 6B:
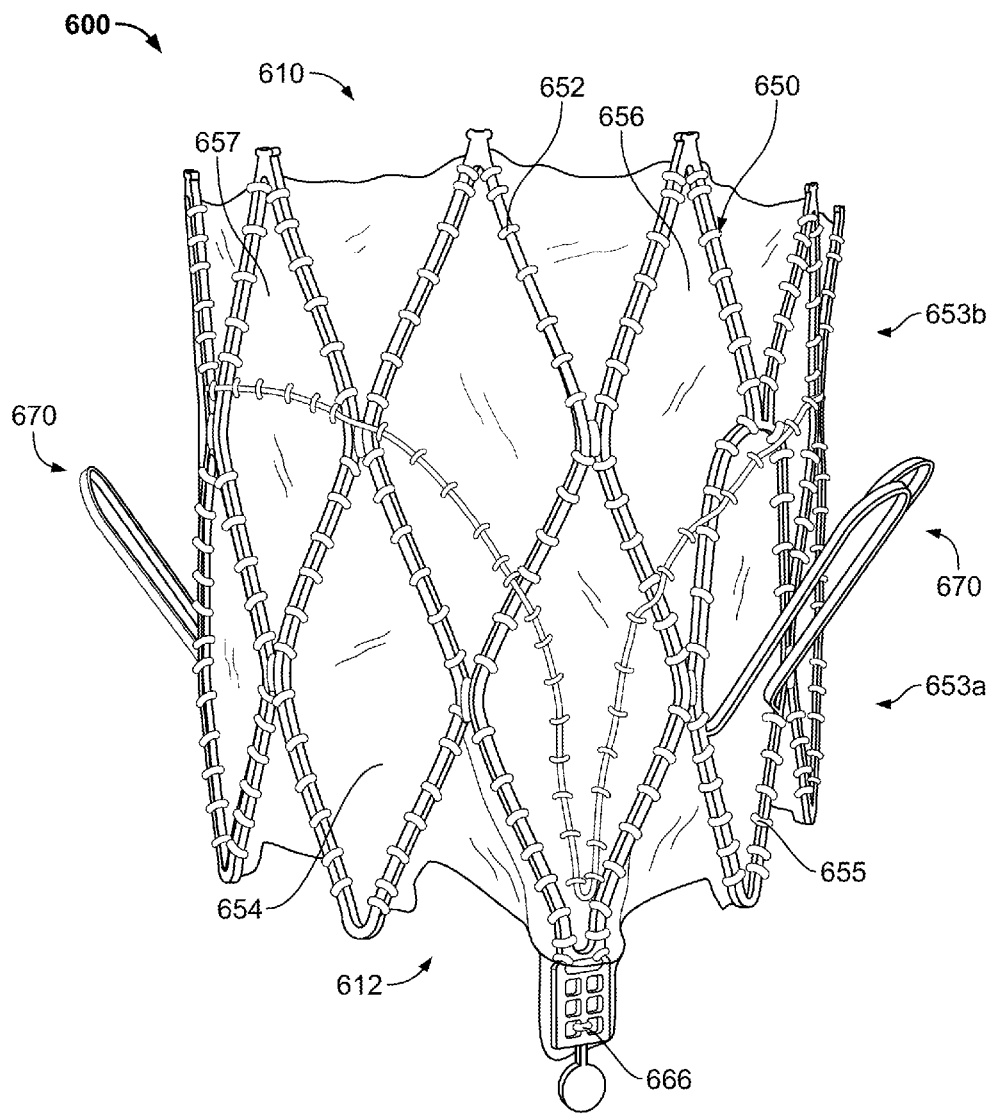
FIG. 6B is a side view of the prosthetic heart valve of FIG. 6A rotated about its longitudinal axis.
Figure 6C:
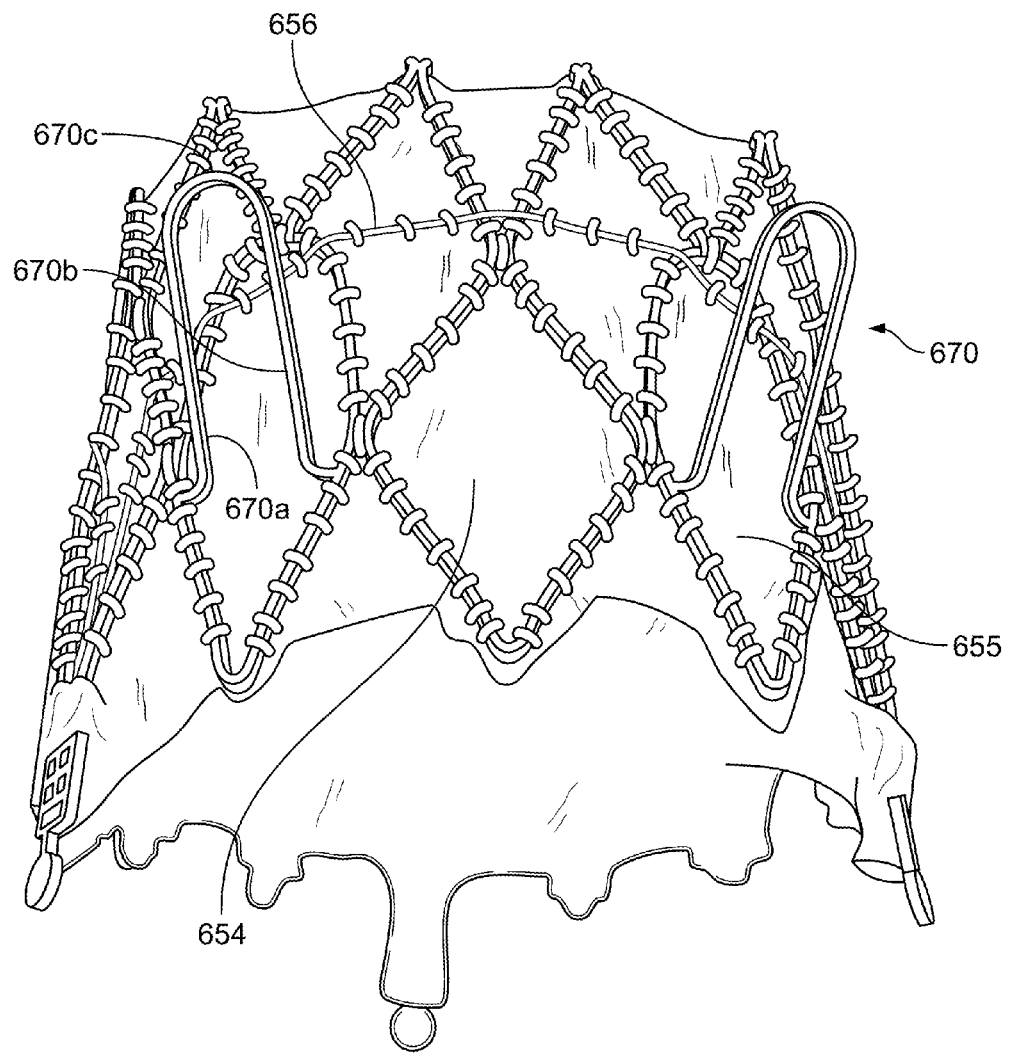
FIG. 6C is a bottom perspective view of the outflow end of the prosthetic heart valve of FIG. 6A.
Figure 6D:
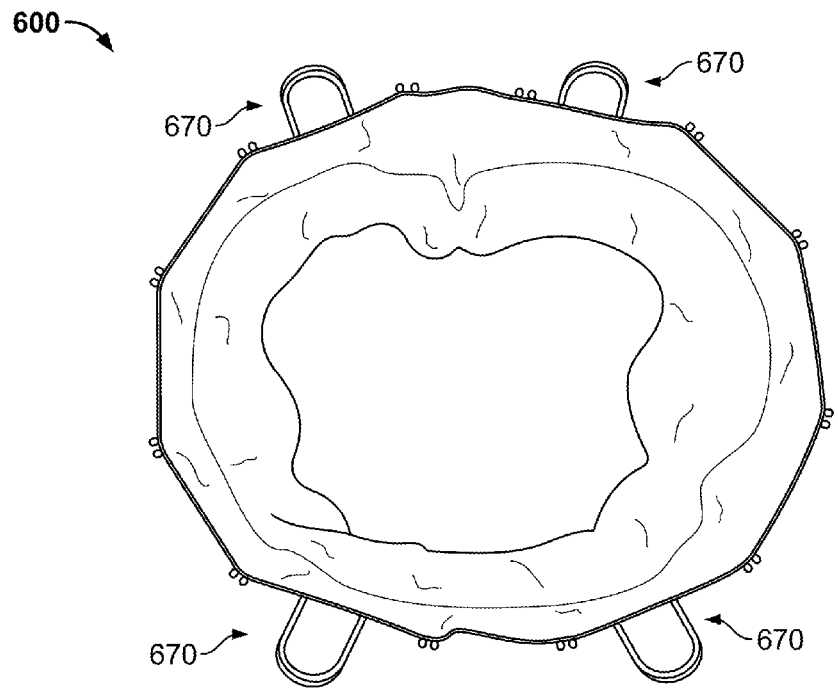
FIG. 6D is a top view of the inflow end of the prosthetic heart valve of FIG. 6A.
Figure 6E:
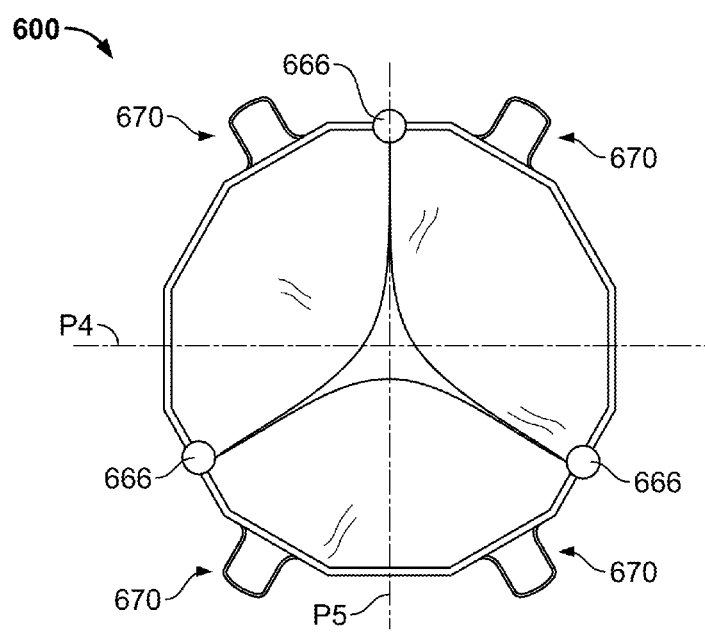
FIG. 6E is a highly schematic bottom view of the outflow end of the prosthetic heart valve of FIG. 6A.

FIG. 6A is a side view of prosthetic heart valve 600 in accordance with a further embodiment of the disclosure. FIG. 6B illustrates prosthetic heart valve 600 rotated approximately 90 degrees about its longitudinal axis compared to FIG. 6A. Prosthetic heart valve 600 may be similar to prosthetic heart valve 300 in certain respects. For example, prosthetic heart valve 600 is collapsible and expandable and designed for replacement of a native mitral valve, having a substantially cylindrical shape with an inflow end 610 and an outflow end 612. Prosthetic heart valve 600 may also include a valve assembly having three leaflets attached to a cylindrical cuff, in substantially the same manner as described above in connection with prosthetic heart valve 400. It should be understood that prosthetic heart valve 600 is not limited to replacement of mitral valves, and may be used to replace other heart valves.

Prosthetic heart valve 600 may include stent 650, which generally extends between inflow end 610 and outflow end 612 and includes a plurality of struts 652 forming two circumferential rows of cells 653a, 653b. CAFs 666 may be included near outflow end 612. First row of cells 653a is disposed adjacent outflow end 612 and includes fully symmetric cells 654 alternating with second cells 655. Fully symmetric cells 654 may be substantially diamond-shaped and include four substantially straight struts 654a-d of equal length. Cells 654 are fully symmetric in that they are symmetric about a vertical line extending from the intersection of struts 654a and 654b to the intersection of struts 654c and 654c, and about a horizontal line extending from the intersection of struts 654a and 654c to the intersection of struts 654b and 654d. Cells 655 may include a pair of substantially straight struts 655a, 655b which form a V-shape attached to two substantially curved struts 655c, 655d. Cells 655 are partially symmetric in that they are symmetric only about a vertical line extending from the intersection of struts 655a and 655b to the intersection of struts 655c and 655d. Engaging arms 670 may be nested within each cell 655. Engaging arms 670 may be pivotably connected to cells 655 and configured to engage portions of heart tissue (e.g., native mitral valve leaflets) when prosthetic heart valve 600 is deployed in a patient, similar to anchor arms 470 described above. Second row of cells 653b may include a plurality of asymmetric cells 656 formed by two struts shared with cells from first row 653a (e.g., struts 654c and 655d or struts 654d and 655c) and two substantially straight struts 656a, 656b. Second row of cells 653b may also include a plurality of fully symmetric cells 657 substantially similar or identical to fully symmetric cells 654.

As shown in FIGS. 6A-E, stent 650 is formed of two rows of cells, each row having twelve cells and is thus referred to as a twelve-cell configuration. The considerations regarding the placement of engaging arms 670 around the circumference of stent 650 are similar to those described above with respect to the placement of anchor arms 470' on twelve-cell stent 450'. In particular, first row of cells 653a may include two sets of three fully symmetric cells 654 on diametrically opposing portions of stent 650. Between each set of fully symmetric cells 654 may be another set of three cells, each set including two partially symmetric cells 655 having engaging arms 670 nested therein with a fully symmetric cell 654 positioned between the two partially symmetric cells 655. Because stent 650 has an even number of cells in first circumferential row 653a, in this case twelve, engaging arms 670 may be positioned symmetrically relative to two planes P4, P5, each bisecting prosthetic heart valve 600.

Each engaging arm 670 may be formed of a shape-memory alloy, and is preferably formed from the same material as stent 650. For example, stent 650 and engaging arms 670 may be formed from a single tube of Nitinol, for example by laser cutting. Engaging arms 670 may include two substantially parallel struts 670a, 670b connected to one another by rounded strut 670c. Engaging arms 670 may be shape set, for example by heat setting, so that in the absence of external forces, the free end of engaging arm 670 defined by strut 670c is positioned radially outwardly from the partially symmetric cell 655 in which the engaging arm is nested. However, forces may be applied to engaging arms 670 and to prosthetic heart valve 600 generally to reduce the radial size and/or bulk of the prosthetic heart valve when in the collapsed condition, which may facilitate intravascular (or other minimally invasive) delivery of the prosthetic heart valve via a delivery device (not shown).

Figure 6F:
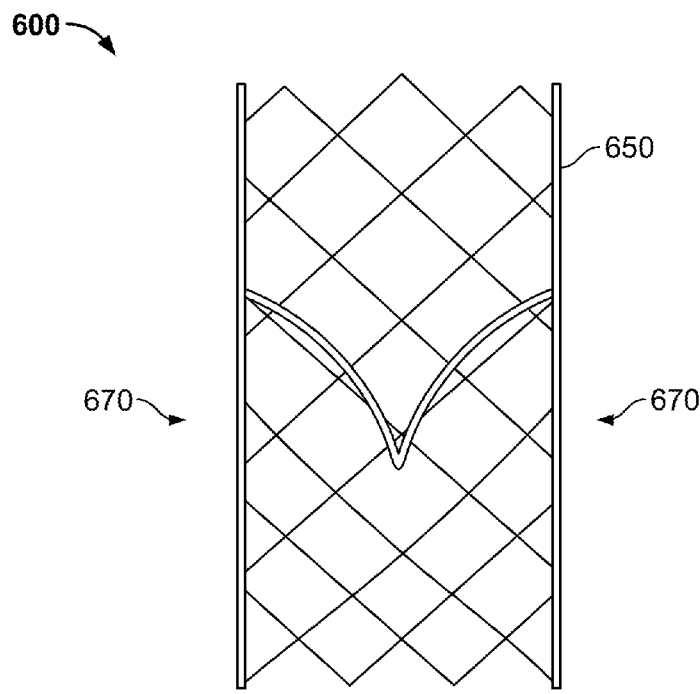
FIG. 6F is a highly schematic longitudinal cross-section of the prosthetic heart valve of FIG. 6A in a collapsed condition.
Figure 6G:
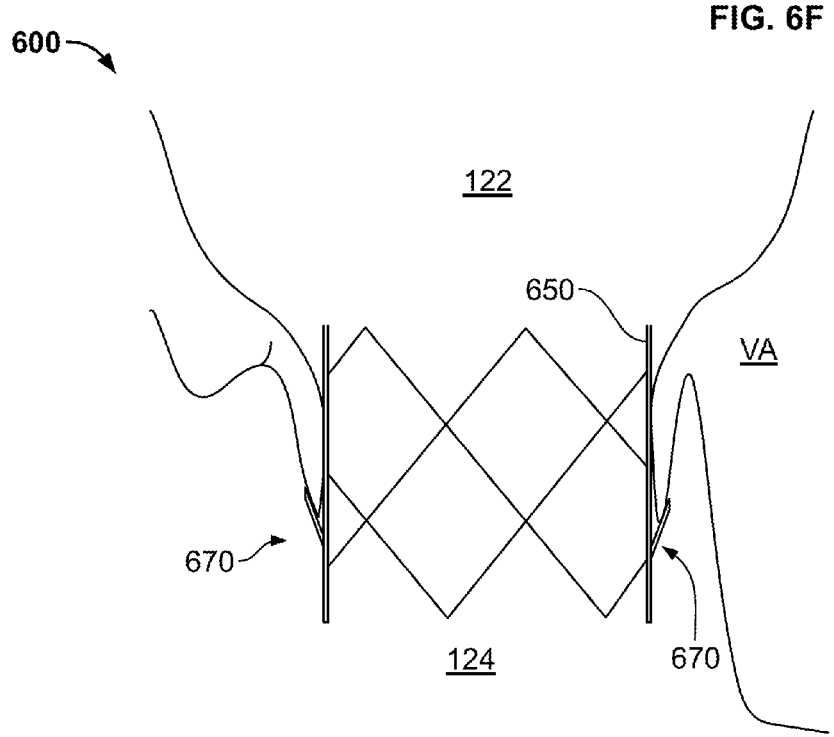
FIG. 6G is a highly schematic representation of the prosthetic heart valve of FIG. 6A implanted into a native mitral valve annulus.

For example, as shown in FIG. 6F, prosthetic heart valve 600 may be transitioned to the collapsed condition, with engaging arms 670 constrained so that each engaging arm is positioned substantially within a surface defined by the partially symmetric cell 655 in which the engaging arm is nested. In other words, when in the collapsed condition shown in FIG. 6F, engaging arms 670 do not protrude a significant distance radially outwardly from stent 650. Prosthetic heart valve 600 may be held in the collapsed condition by the delivery device as it is delivered to native mitral valve 130. When in a desired position relative to native mitral valve 130, prosthetic heart valve 600 may be released from the delivery device. As constraining forces are removed from prosthetic heart valve 600, it begins to transition to the expanded condition, while engaging arms 670 move to their preset shape projecting radially outwardly from the rest of stent 650. Once engaging arms 670 are in their preset shape, prosthetic heart valve 600 may be pulled (or pushed) toward left atrium 122 until engaging arms 670 hook under native mitral valve leaflets 136, 138, as shown in FIG. 6G. The rounded configuration of strut 670c may reduce the likelihood of trauma to native tissue captured by engaging arms 670. When hooked around native mitral valve leaflets 136, 138, engaging arms 670 help anchor prosthetic heart valve 600 within native valve annulus VA and resist its migration into left atrium 122.

Figure 7A:
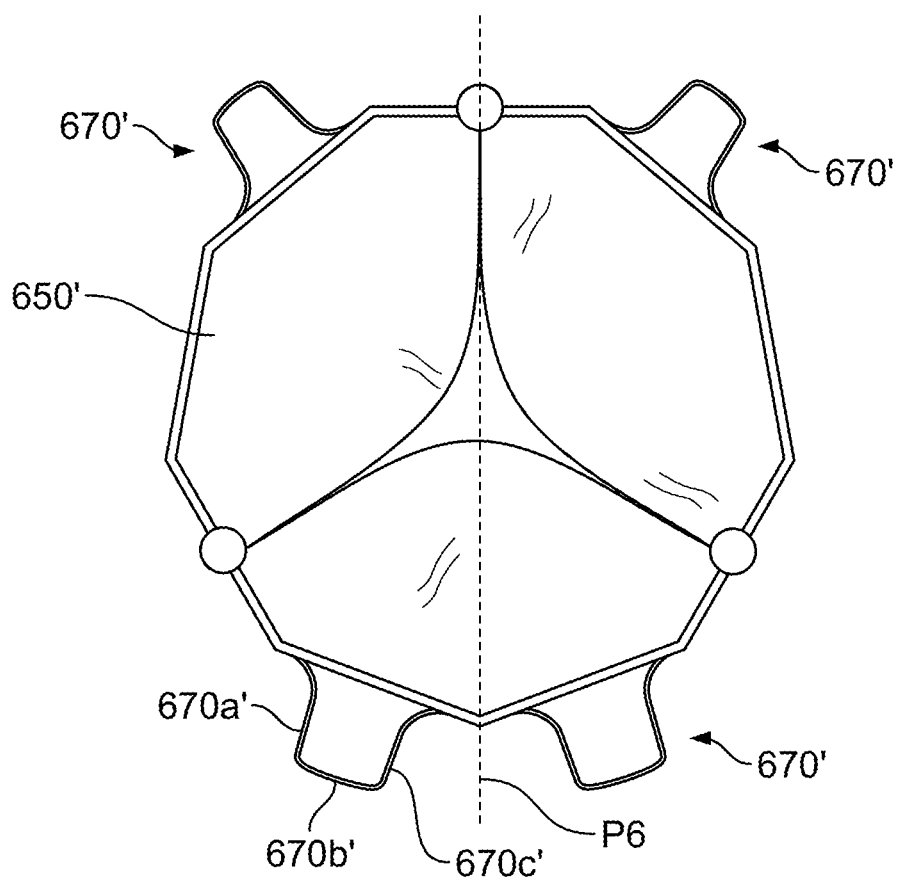
FIG. 7A is a highly schematic bottom view of the outflow end of a prosthetic heart valve according to another aspect of the disclosure.
Figure 7C:
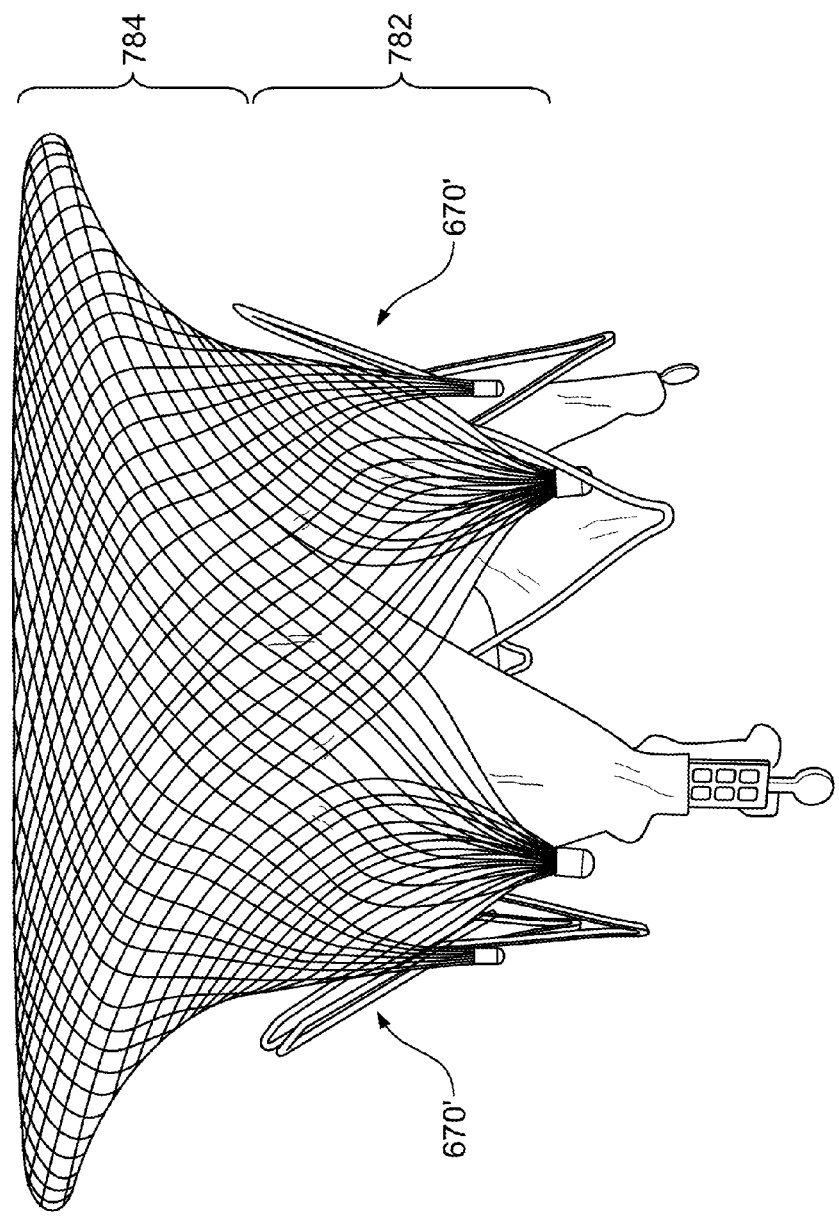
FIG. 7C is a side view of the prosthetic heart valve of FIG. 7B rotated about its longitudinal axis.
Figure 7D:
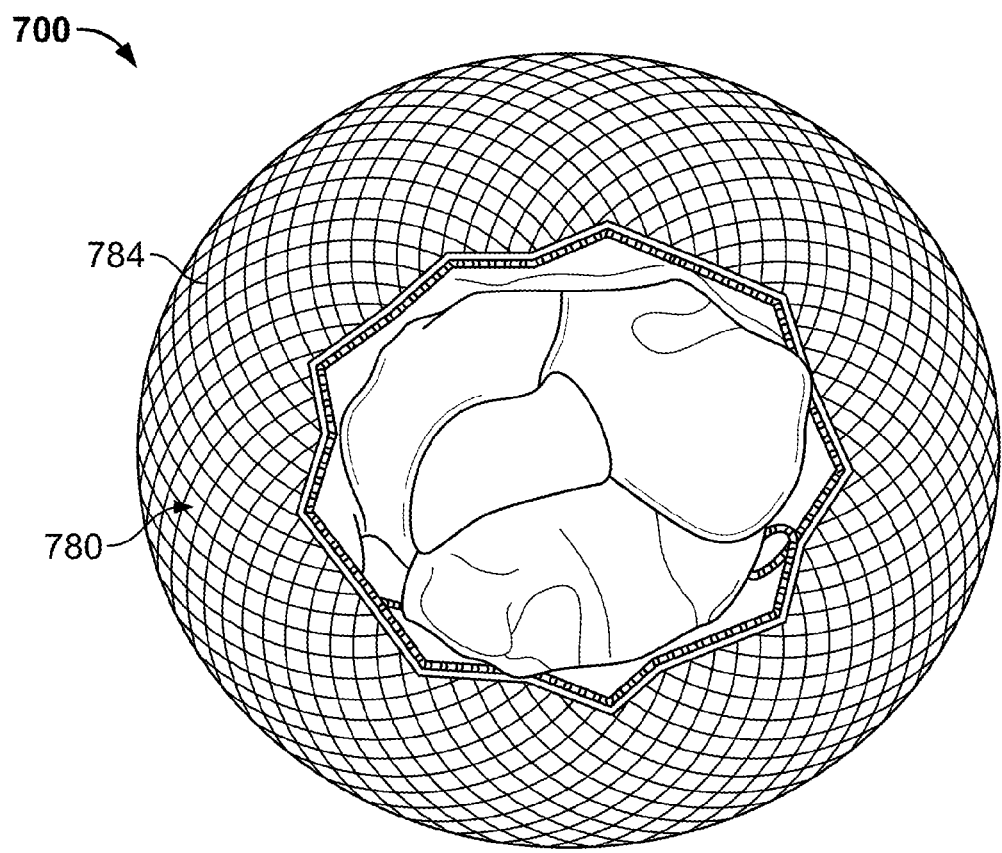
FIG. 7D is a top view of the inflow end of the prosthetic heart valve of FIG. 7B.
Figure 7E:
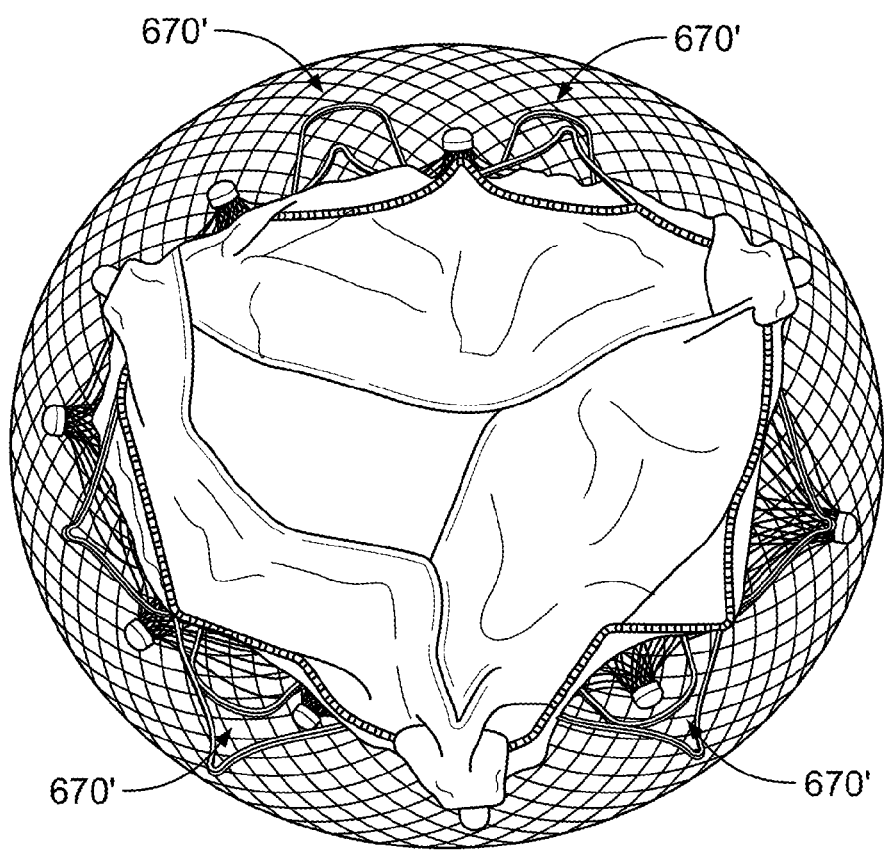
FIG. 7E is a bottom view of the outflow end of the prosthetic heart valve of FIG. 7B.
Figure 7F:
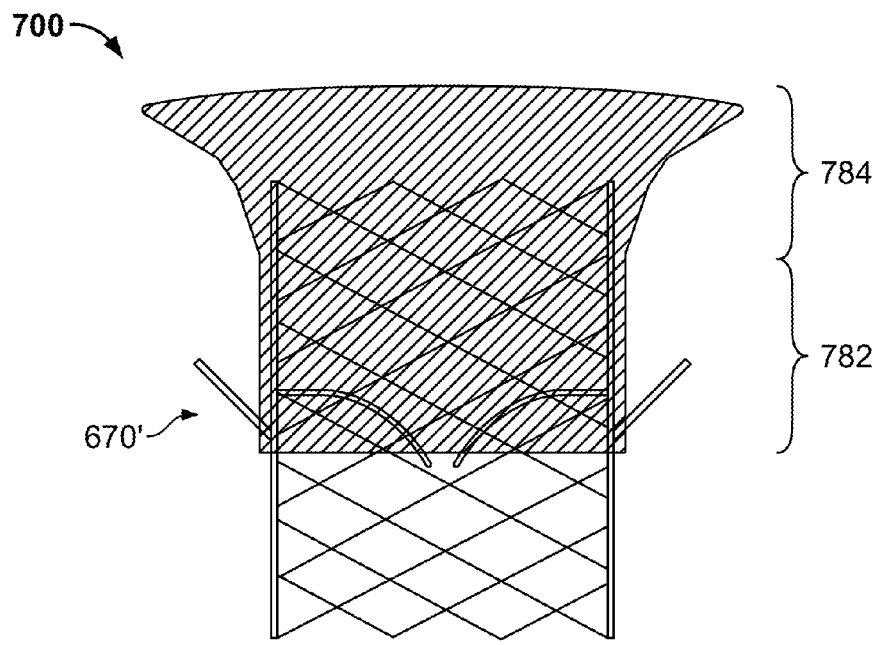
FIG. 7F is a highly schematic longitudinal cross-section of the prosthetic heart valve of FIG. 7B in the expanded condition.

Similar to stent 450, stent 650 of prosthetic heart valve 600 may be formed with an odd number of cells in each circumferential row rather than an even number. Stent 650', shown in FIG. 7A, is similar to stent 650 with the exception that it has two annular rows of nine cells each. With this configuration, engaging arms 670' may be situated around the circumference of stent 650' so that they are symmetric relative to one plane P6. Prosthetic heart valve 700, shown in FIGS. 7B-H, incorporates flange 780 with stent 650'. Flange 780, and its relation to stent 650', may be similar or identical to flange 580 of prosthetic heart valve 500 and its relation to stent 450'. For example, flange 780 may include a plurality of braided strands or wires 786 arranged in three dimensional shapes. The body portion 782 and flared portion 784 of flange 780 may also be similar or identical to the corresponding portions of flange 580, with body portion 782 being coupled to stent 650' by sutures, for example. Similar to prosthetic heart valve 500, engaging arms 670' of prosthetic heart valve 700 are shape-set so that, in the absence of applied forces, body 782 of flange 780 is positioned between the struts 670a'-670c' forming engaging arms 670' and the remainder of stent 650'. Similarly, prosthetic heart valve 700 may also include a valve assembly having three leaflets attached to a cylindrical cuff, in substantially the same manner as described above in connection with prosthetic heart valves 400 and 600.

Figure 7G:
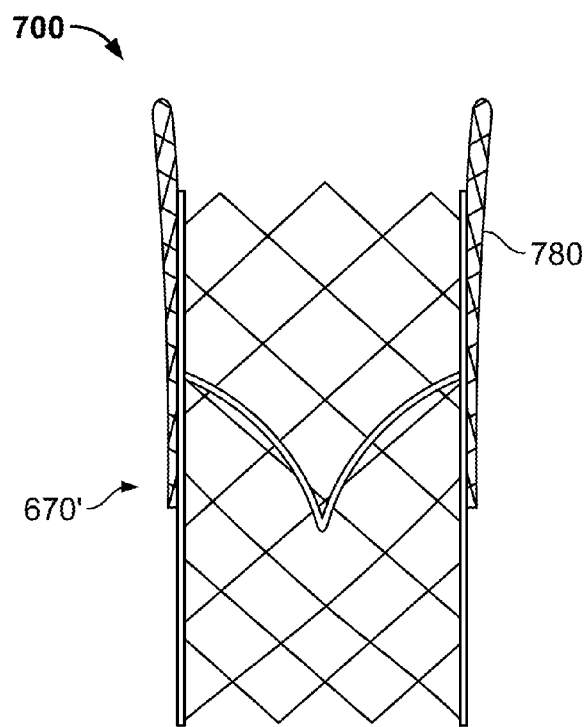
FIG. 7G is a highly schematic longitudinal cross-section of the prosthetic heart valve of FIG. 7B in the collapsed condition.
Figure 7H:
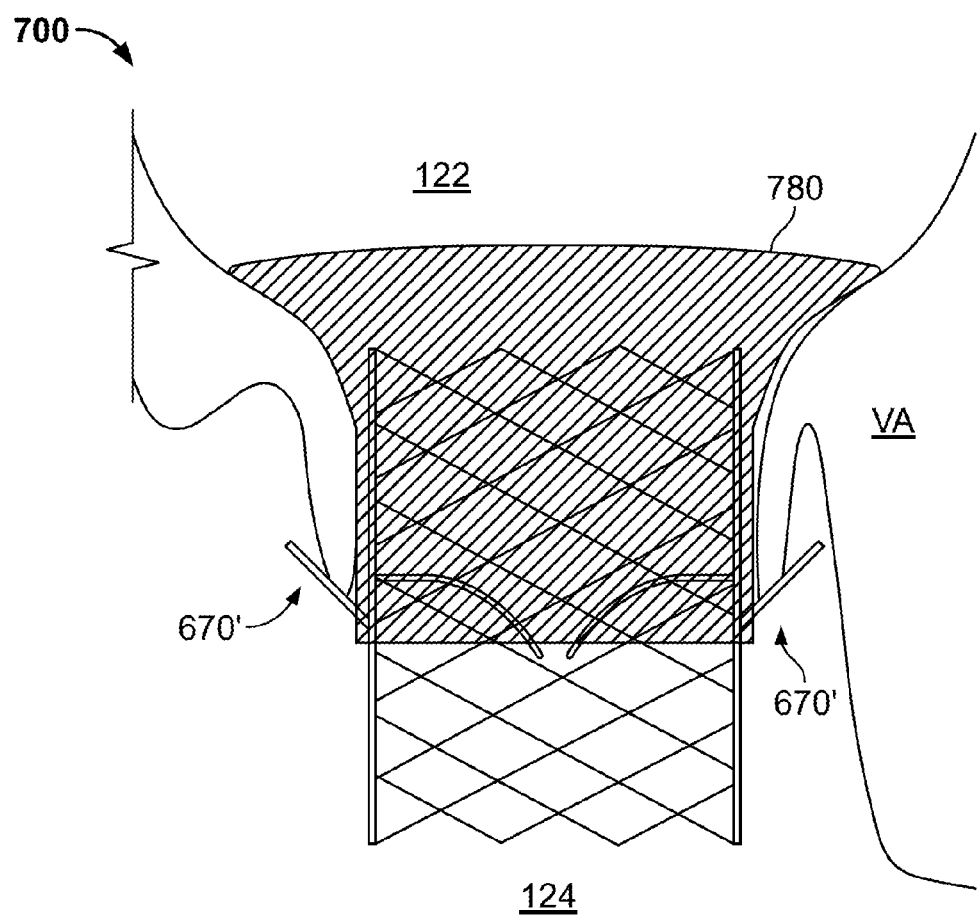
FIG. 7H is a highly schematic representation of the prosthetic heart valve of FIG. 7B implanted into a native mitral valve annulus.

Prosthetic heart valve 700 may be delivered to the implant site in the collapsed condition, shown in FIG. 7G, and transitioned to the expanded condition near native mitral valve 130. Engaging arms 670' revert to the preset shape in a similar manner as described above in connection with the engaging arms of prosthetic heart valve 600, capturing native mitral valve leaflets 136, 138 between engaging arms 670' and corresponding portions of stent 650', as shown in FIG. 7H. Flange 780 also transitions from the collapsed condition to the expanded condition, assuming its preset shape shown in FIG. 7H. Similar to flange 580 of prosthetic heart valve 500, flange 780 of prosthetic heart valve 700 expands to help anchor prosthetic valve 700 within native valve annulus VA. Flange 780 may also include a fabric layer, similar to fabric layer 588, to provide additional sealing against PV leak. As with prosthetic heart valve 500 described above, the combination of engaging arms 670' and flange 780 securely anchors prosthetic heart valve 700 within native valve annuls VA and limits its migration toward either the left atrium or the left ventricle.

A prosthetic heart valve 800 according to still another embodiment of the disclosure, and a stent 850 for use prosthetic heart valve 800, are illustrated in FIGS. 8A-H. Prosthetic heart valve 800 may be similar to prosthetic heart valve 700, but incorporates a flared stent rather than a braided flange, as described below. As should be understood, prosthetic heart valve 800 may also include a valve assembly having three leaflets attached to a cylindrical cuff, in substantially the same manner as described above in connection with prosthetic heart valves 400, 600, and 700.

Figure 8A:
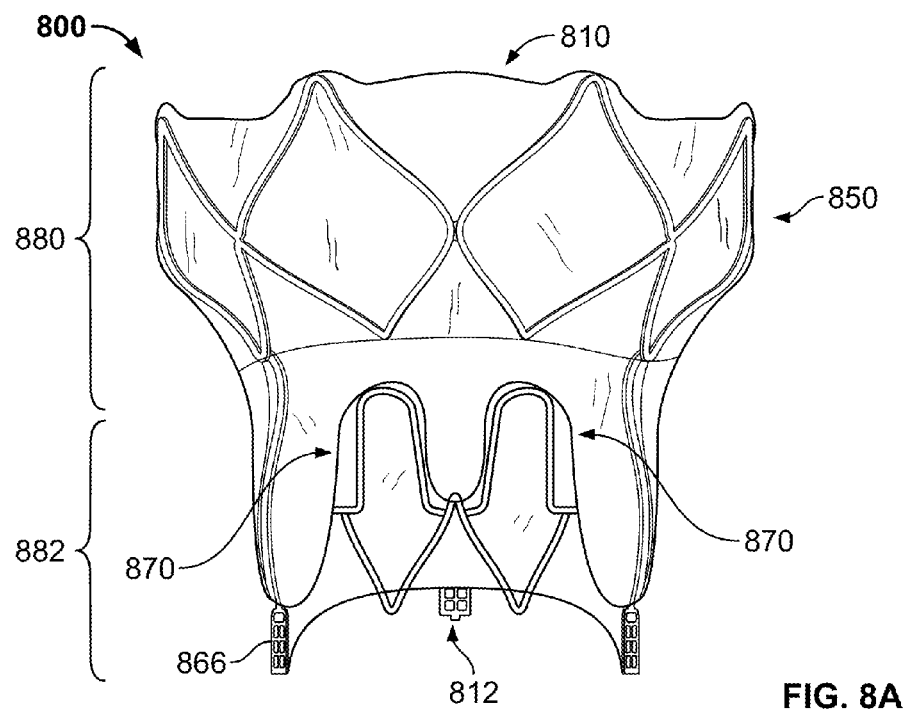
FIG. 8A is a side view of a prosthetic heart valve according to yet another aspect of the disclosure.

FIG. 8A is side view of prosthetic heart valve 800. Prosthetic heart valve 800 is collapsible and expandable and designed for replacement of a native mitral valve. Prosthetic heart valve 800 has an inflow end 810, an outflow end 812, a substantially cylindrical portion nearer outflow end 812, and a flared portion nearer inflow end 810 when in the expanded condition. It should be understood that prosthetic heart valve 800 is not limited to replacement of mitral valves, and may be used to replace other heart valves.

Figure 8B:
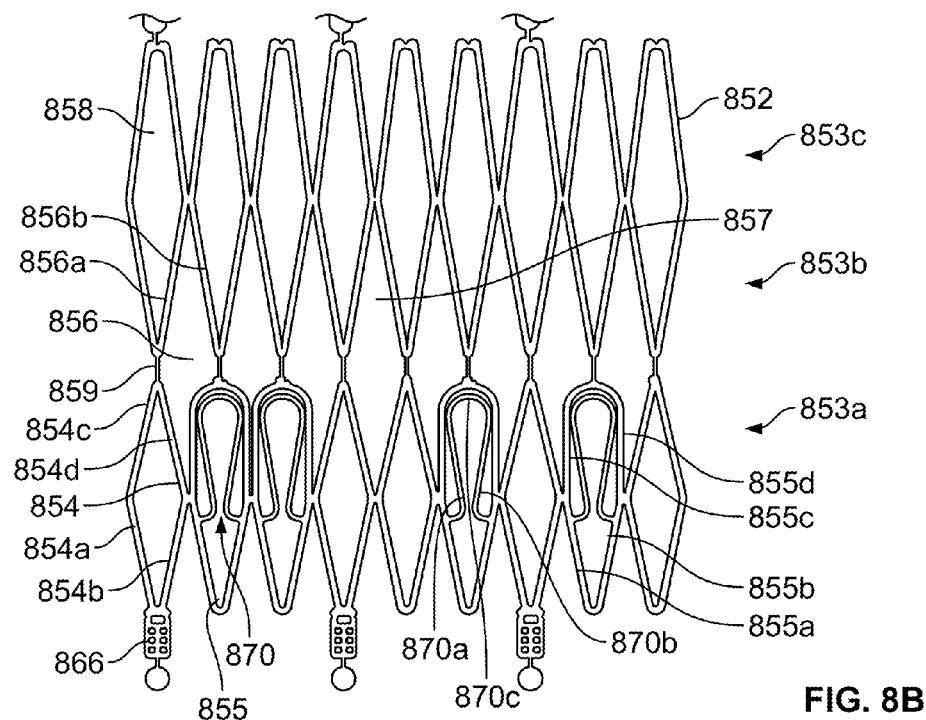
FIG. 8B is a developed view of a stent used in the prosthetic heart valve of FIG. 8A.
Figure 8C:
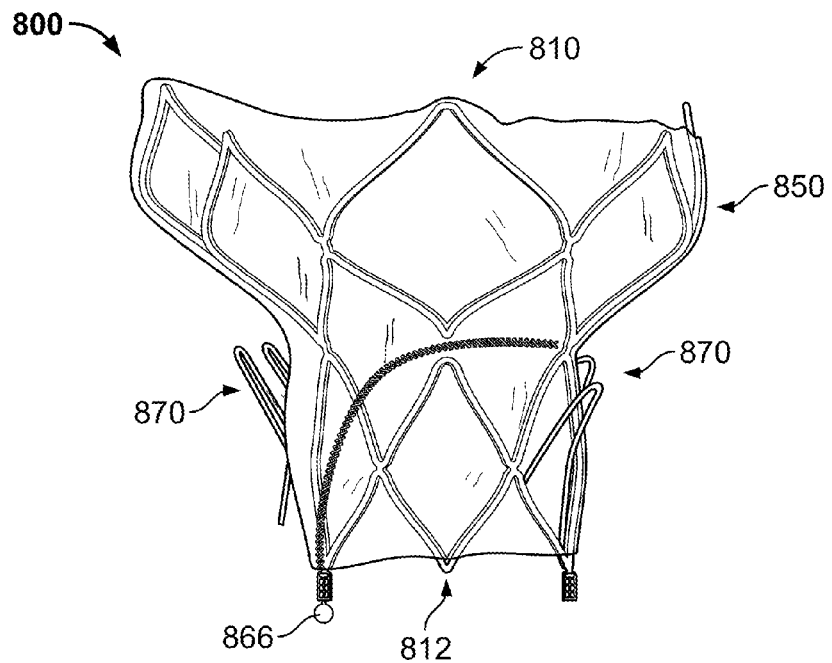
FIG. 8C is a side view of the prosthetic heart valve of FIG. 8A rotated about its longitudinal axis.
Figure 8D:
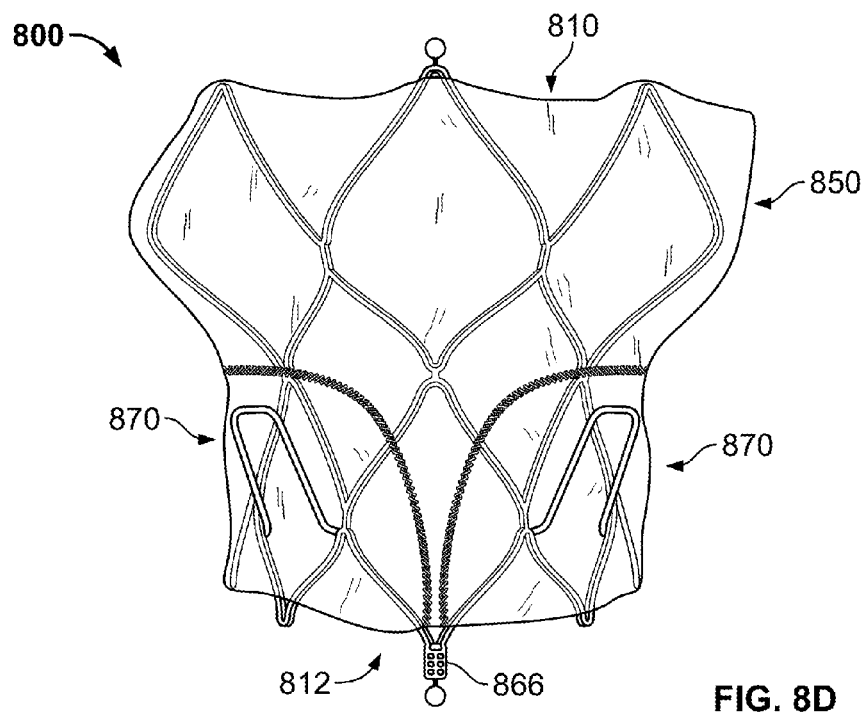
FIG. 8D is a side view of the prosthetic heart valve of FIG. 8A rotated further about its longitudinal axis.
Figure 8E:
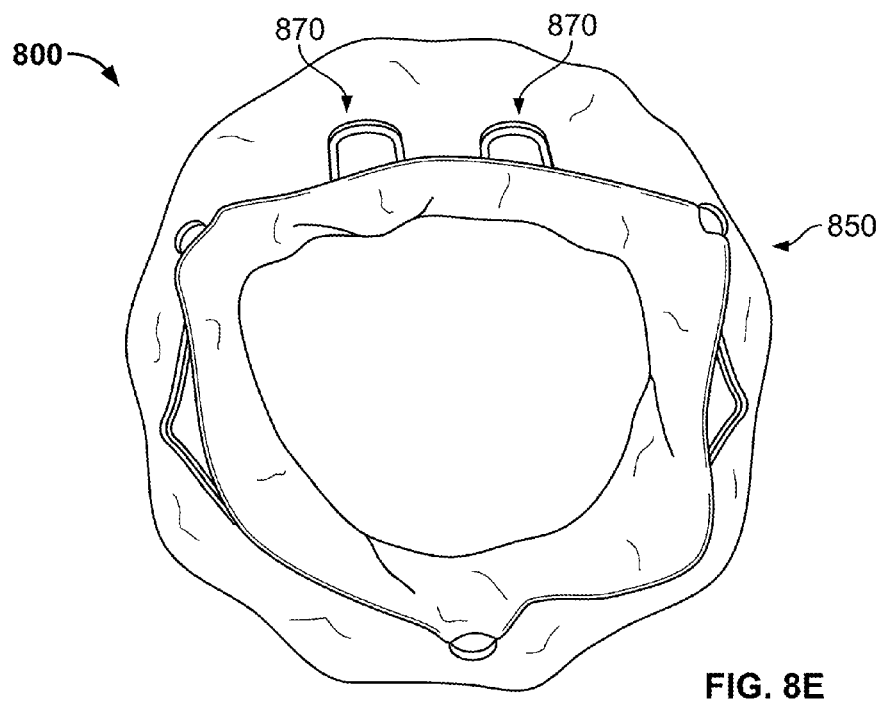
FIG. 8E is a bottom view of the outflow end of the prosthetic heart valve of FIG. 8A.
Figure 8F:
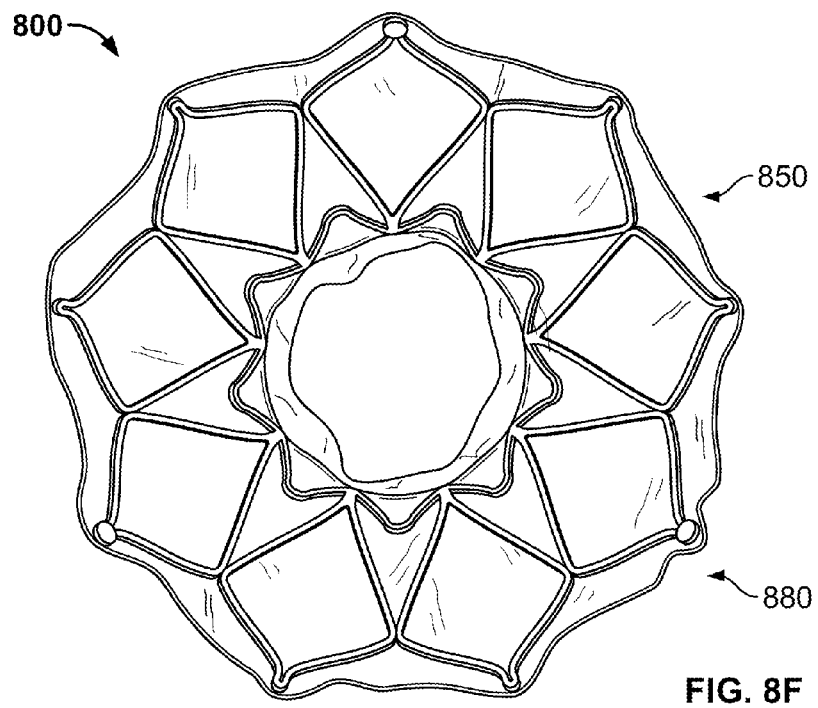
FIG. 8F is a top view of the inflow end of the prosthetic heart valve of FIG. 8A.

Prosthetic heart valve 800 includes stent 850, which has similar securement features as prosthetic heart valves 600 and 700 described above. In particular, and as best shown in FIG. 8B, stent 850 includes a plurality of struts 852 forming three circumferential rows of cells 853a, 853b, and 853c. CAFs 866 may be included near outflow end 812. First row of cells 853a is disposed adjacent outflow end 812 and includes fully symmetric cells 854 and partially symmetric cells 855 at selected positions within first row 853a, similar to the first row of cells 653a of prosthetic heart valve 600. Fully symmetric cells 854 may be substantially diamond-shaped and include four substantially straight struts 854a-d of equal length. Cells 854 are fully symmetric in that they are symmetric about a vertical line extending from the intersection of struts 854a and 854b to the intersection of struts 854c and 854c, and about a horizontal line extending from the intersection of struts 854a and 854c to the intersection of struts 854b and 854d. Cells 855 may include a pair of substantially straight struts 855a, 855b which form a V-shape attached to two substantially curved struts 855c, 855d. Cells 855 are partially symmetric in that they are symmetric only about a vertical line extending from the intersection of struts 855a and 855b to the intersection of struts 855c and 855d. Engaging arms 870 may be nested within each cell 855. Engaging arms 870 are pivotably connected to cells 855 and may be configured to engage portions of heart tissue (e.g., native mitral valve leaflets) when prosthetic heart valve 800 is deployed in a patient, similar to engaging arms 670 described above. Second row of cells 853b may include a plurality of asymmetric cells 856 formed by two struts shared with cells from first row 853a (e.g., struts 854c and 855d or struts 854d and 855c) and two substantially straight struts 856a, 856b. Cells 856 may also include runners 859, which connect cells 858 to adjacent cells 854 or 855. Second row of cells 853b may also include one or more fully symmetric cells 857 substantially similar or identical to fully symmetric cells 854, although the dimensions of fully symmetric cells 857 may be different than those of fully symmetric cells 854. Third row of cells 853c is positioned adjacent inflow end 810 and may include a plurality of enlarged substantially diamond-shaped cells 858 that provide a flared shape when prosthetic heart valve 800 is in the expanded condition, as described in greater detail below. It should also be noted that the ends of cells 858 nearest inflow end 810 may be blunted or otherwise rounded, rather than V-shaped.

As shown in FIGS. 8A-D, the three rows of cells forming stent 850 each have nine cells. The considerations regarding the placement of engaging arms 870 around the circumference of stent 850 are similar to those previously discussed with respect to prosthetic heart valve 700, which also has a nine-cell configuration. However, it should be understood that prosthetic heart valve 800 may alternatively take a configuration with a different odd number of cells, or an even number of cells, such as a twelve-cell configuration in which the engaging arms are placed at positions substantially similar to those for prosthetic heart valve 600, shown in FIG. 6E and described above. As shown, first row of cells 853a may include two partially symmetric cells 855 adjacent to one another, each having an engaging arm 870 nested therein. First row of cells 853a may also include, substantially diametrically opposed to adjacent cells 855, two additional partially symmetric cells 855 separated by a single fully symmetric cell 854, each of the two additional partially symmetric cells 855 having an engaging arm 870 nested therein.

The structure of engaging arms 870 may be substantially similar to the structure of engaging arms 670. In other words, each engaging arm 870 may be formed of a shape-memory alloy, and is preferably formed from the same material as stent 850. Engaging arms 870 may include two substantially parallel struts 870a, 870b connected to one another by rounded strut 870c. Engaging arms 870 may be shape set in a similar manner to engaging arms 670 so that the free end of each engaging arm 870 defined by rounded strut 870c is positioned radially outwardly from the partially symmetric cell 855 in which the engaging arm is nested. However, forces may be applied to engaging arms 870 and to prosthetic heart valve 800 generally to reduce the radial size and/or bulk of the prosthetic heart valve when in the collapsed condition, which may facilitate intravascular (or other minimally invasive) delivery of the prosthetic heart valve via a delivery device (not shown).

In the expanded condition of prosthetic heart valve 800, the cells in the third row 853c and portions of the cells in the second row 853b flare radially outwardly to form a flared section 880. At the same time, the cells in the first row 853a and other portions of the cells in the second row 853b form a substantially cylindrical section 882. With this expanded configuration, the diameter of inflow end 810 of stent 850 is greater than the diameter of outflow end 812. Flared section 880 may function to help anchor prosthetic heart valve 800 in native mitral valve annulus VA and to prevent PV leak, as described in greater detail below, in a manner similar to the flanges described above in connection with prosthetic heart valves 500 and 700.

Figure 8G:
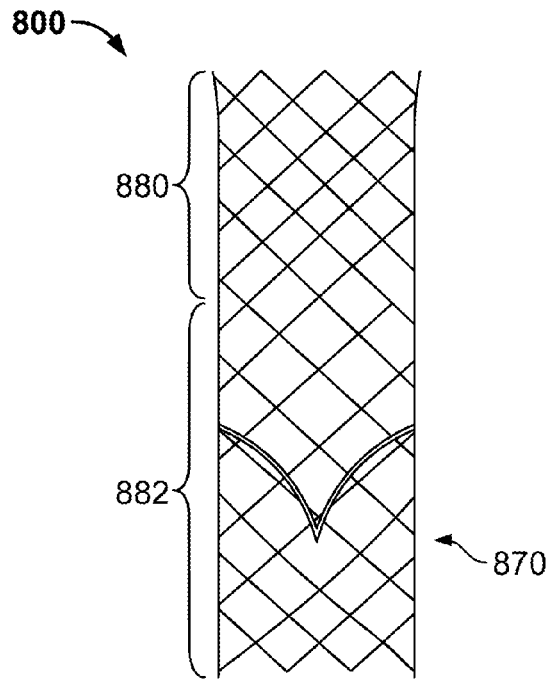
FIG. 8G is a highly schematic longitudinal cross-section of the prosthetic heart valve of FIG. 8A in a collapsed condition.
Figure 8H:
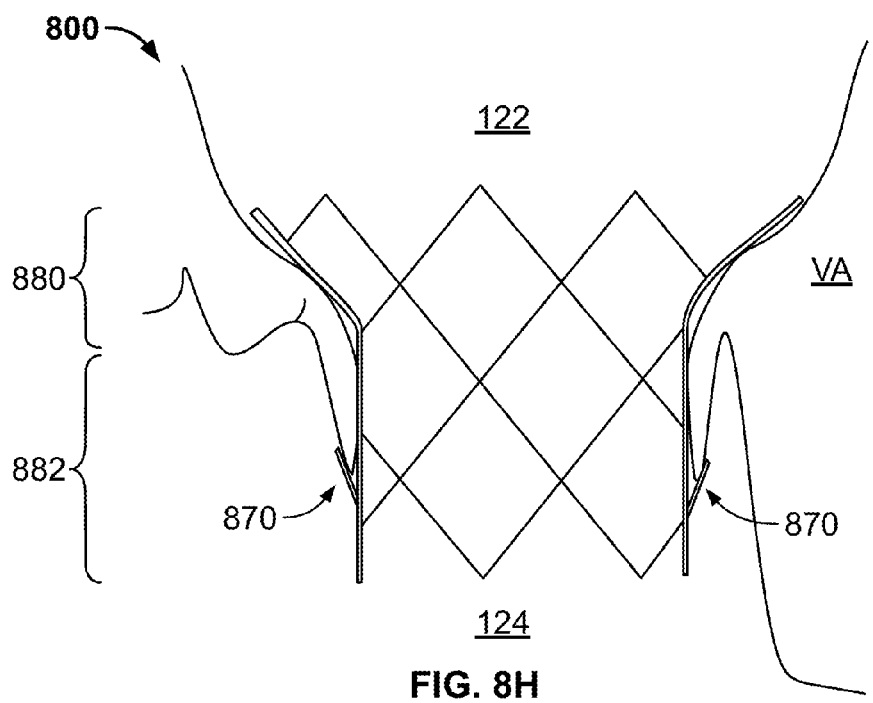
FIG. 8H is a highly schematic representation of the prosthetic heart valve of FIG. 8A implanted into a native mitral valve annulus.

As shown in FIG. 8G, prosthetic heart valve 800 may be transitioned to the collapsed condition, with engaging arms 870 constrained so that each engaging arm 870 is positioned substantially within a surface defined by the partially symmetric cell 855 in which the engaging arm is nested. Flared section 880 may also collapse to a substantially cylindrical profile. Prosthetic heart valve 800 may be held in the collapsed condition by the delivery device as it is delivered to native mitral valve 130. When positioned as desired relative to native mitral valve 130, prosthetic heart valve 800 may be released from the delivery device. As constraining forces are removed from prosthetic heart valve 800, it begins to transition to the expanded condition, while engaging arms 870 and flared section 880 revert to their preset shapes projecting radially outwardly from the rest of stent 850. Once engaging arms 870 are in their preset shape, prosthetic heart valve 800 may be pulled (or pushed) toward left atrium 122 until engaging arms 870 hook under native mitral valve leaflets 136, 138, as shown in FIG. 8H. It is preferable that the pair of engaging arms 870 nested within immediately adjacent partially symmetric cells 855 be hooked under posterior leaflet 136 of native mitral valve 130, with the pair of engaging arms 870 separated by a fully symmetric cell 854 being hooked under anterior leaflet 138 of native mitral valve 130. With this configuration, two CAFs 866 abut posterior leaflet 136 and one CAF abuts anterior leaflet 138. It should be understood that in this embodiment, as well as in other embodiments, the positioning of the prosthetic heart valve 800 may alternatively be such that two CAFs 866 abut anterior leaflet 138 and one CAF 866 abuts posterior leaflet 136. As flared section 880 transitions from the collapsed condition to the expanded condition, it begins to expand radially outwardly to the shape illustrated in FIG. 8A. When implanted and in the expanded condition, flared section 880 provides a large surface area to help anchor prosthetic valve 800 within native valve annulus VA, and may be particularly effective at resisting movement of prosthetic heart valve 800 toward left ventricle 124. Specifically, flange 880 has an expanded diameter that is too large to pass through native valve annulus VA. It will therefore be apparent that the combination of engaging arms 870 and flange 880 helps securely anchor prosthetic heart valve 800 within the mitral valve annulus VA and limit its migration toward either the left ventricle of the left atrium.

According to one aspect of the disclosure, a prosthetic heart valve having an inflow end and an outflow end, comprises:

a stent having a collapsed condition, an expanded condition, and a plurality of cells arranged in circumferential rows;

an anchor arm having a body portion and a free end extending from the body portion, the body portion being coupled to a perimeter of one of the plurality of cells, and the free end extending toward the inflow end at a spaced distance radially outward from the body portion in an expanded condition of the anchor arm; and a valve assembly disposed within the stent and having a plurality of leaflets; and/or the anchor arm comprises a wire, the body portion being formed by a center portion of the wire and the free end comprising two end portions of the wire on opposite sides of the center portion; and/or the anchor arm includes an atraumatic end cap coupled to the two end portions of the wire; and/or the anchor arm is sutured to the one cell; and/or the one cell has a shape in the expanded condition of the stent and the body portion of the anchor arm has a shape in the expanded condition of the anchor arm that is substantially the same as the cell shape; and/or the one cell is substantially diamond-shaped in the expanded condition of the stent and the body portion of the anchor arm is substantially diamond-shaped in the expanded condition of the anchor arm; and/or a flange formed of a braided mesh and having a body portion coupled to the stent and a flared portion adjacent the inflow end of the prosthetic heart valve; and/or the flared portion of the flange has a first diameter in an expanded condition of the flange and the body portion of the flange has a second diameter in the expanded condition of the flange smaller than the first diameter; and/or the flange includes a first braided mesh layer, a second braided mesh layer, and a layer of fabric between the first layer and the second layer; and/or the flared portion of the flange terminates at an inflow end of the flange and the body portion of the flange terminates at an outflow end of the flange, the outflow end of the flange being positioned between the free end portion of the anchor arm and the body portion of the anchor arm in the expanded condition of the stent; and/or the plurality of cells include an odd number of cells arranged in a first circumferential row, four anchor arms being positioned in the first circumferential row so that a first pair of the anchor arms is symmetrical to a second pair of the anchor arms relative to a plane bisecting the prosthetic heart valve; and/or the plurality of cells include an even number of cells arranged in a first circumferential row, four anchor arms being positioned in the first circumferential row so that a first pair of the anchor arms is symmetrical to a second pair of the anchor arms relative to a first plane bisecting the prosthetic heart valve, and a third pair of the anchor arms is symmetrical to a fourth pair of the anchor arms relative to a second plane orthogonal to the first plane.

According to another aspect of the disclosure, a prosthetic heart valve having an inflow end and an outflow end, comprises:

a stent having a collapsed condition, an expanded condition, and a plurality of cells arranged in circumferential rows;

an engaging arm pivotably disposed in one of the plurality of cells adjacent the outflow end, the engaging arm having a first strut coupled to the one cell, a second strut coupled to the one cell, and a third curved strut coupling the first strut to the second strut;

a flange formed of a braided mesh and having a body portion coupled to the stent and a flared portion adjacent the inflow end of the prosthetic heart valve; and a valve assembly disposed within the stent and having a plurality of leaflets; and/or the third strut defines a free end of the engaging arm extending toward the inflow end of the prosthetic heart valve; and/or the free end of the engaging arm extends radially outwardly from the one cell in the expanded condition of the stent;

the flared portion of the flange terminates at an inflow end of the flange and the body portion of the flange terminates at an outflow end of the flange, the outflow end of the flange being positioned between the free end of the engaging arm and the one cell in the expanded condition of the stent; and/or the flared portion of the flange has a first diameter in an expanded condition of the flange and the body portion of the flange has a second diameter in the expanded condition of the flange smaller than the first diameter; and/or the flange includes a first braided mesh layer, a second braided mesh layer, and a layer of fabric between the first layer and the second layer; and/or the plurality of cells include an odd number of cells arranged in a first circumferential row, four engaging arms being positioned in the first circumferential row so that a first pair of the engaging arms is symmetrical to a second pair of the engaging arms relative to a plane bisecting the prosthetic heart valve; and/or the plurality of cells include an even number of cells arranged in a first circumferential row, four engaging arms being positioned in the first circumferential row so that a first pair of the engaging arms is symmetrical to a second pair of the engaging arms relative to a first plane bisecting the prosthetic heart valve, and a third pair of the engaging arms is symmetrical to a fourth pair of the engaging arms relative to a second plane orthogonal to the first plane.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims. In addition, features of embodiments described herein may be combined with features of other embodiments described herein without departing from the scope of the invention.

The invention claimed is:

1. A prosthetic heart valve having an inflow end and an outflow end, comprising:

a stent having a collapsed condition, an expanded condition, and a plurality of cells arranged in circumferential rows;

an anchor arm having a body portion and a free end extending from the body portion, the body portion of the anchor arm being coupled to a perimeter of one of the plurality of cells, and the free end extending toward the inflow end at a spaced distance radially outward from the body portion in an expanded condition of the anchor arm;

a valve assembly disposed within the stent and having a plurality of leaflets; and a flange formed of a braided mesh and having a body portion coupled to the stent and a flared portion adjacent the inflow end of the prosthetic heart valve, the body portion of the flange being positioned closer to the outflow end of the stent than is a terminal edge of the flared portion in the expanded condition of the stent, wherein the one cell has a shape in the expanded condition of the stent and the body portion of the anchor arm has a shape in the expanded condition of the anchor arm that is substantially the same as the cell shape.

2. The prosthetic heart valve of claim 1, wherein the anchor arm comprises a wire, the body portion of the anchor arm being formed by a center portion of the wire and the free end comprising two end portions of the wire on opposite sides of the center portion.

3. The prosthetic heart valve of claim 2, wherein the anchor arm includes an atraumatic end cap coupled to the two end portions of the wire.

4. The prosthetic heart valve of claim 1, wherein the anchor arm is sutured to the one cell.

5. The prosthetic heart valve of claim 1, wherein the one cell is substantially diamond-shaped in the expanded condition of the stent and the body portion of the anchor arm is substantially diamond-shaped in the expanded condition of the anchor arm.

6. The prosthetic heart valve of claim 1, wherein the flared portion of the flange has a first diameter in an expanded condition of the flange and the body portion of the flange has a second diameter in the expanded condition of the flange smaller than the first diameter, a diameter of the flange continuously increasing from the second diameter to the first diameter in a longitudinal direction from the outflow end of the prosthetic heart valve toward the inflow end of the prosthetic heart valve.

7. The prosthetic heart valve of claim 1, wherein the flange includes a first braided mesh layer, a second braided mesh layer, and a layer of fabric between the first layer and the second layer.

8. The prosthetic heart valve of claim 1, wherein the flared portion of the flange terminates at an inflow end of the flange and the body portion of the flange terminates at an outflow end of the flange, the outflow end of the flange being positioned between the free end portion of the anchor arm and the body portion of the anchor arm in the expanded condition of the stent.

9. The prosthetic heart valve of claim 1, wherein the plurality of cells include an odd number of cells arranged in a first circumferential row, four anchor arms being positioned in the first circumferential row so that a first pair of the anchor arms is symmetrical to a second pair of the anchor arms relative to a plane bisecting the prosthetic heart valve.

10. The prosthetic heart valve of claim 1, wherein the plurality of cells include an even number of cells arranged in a first circumferential row, four anchor arms being positioned in the first circumferential row so that a first pair of the anchor arms is symmetrical to a second pair of the anchor arms relative to a first plane bisecting the prosthetic heart valve, and a third pair of the anchor arms is symmetrical to a fourth pair of the anchor arms relative to a second plane orthogonal to the first plane.

11. A prosthetic heart valve having an inflow end and an outflow end, comprising:

a stent having a collapsed condition, an expanded condition, and a plurality of cells arranged in circumferential rows;

an anchor arm having a body portion and a free end extending from the body portion, the body portion of the anchor arm being coupled to a perimeter of one of the plurality of cells, and the free end extending toward the inflow end at a spaced distance radially outward from the body portion in an expanded condition of the anchor arm;

a valve assembly disposed within the stent and having a plurality of leaflets, and a flange formed of a braided mesh and having a body portion coupled to the stent and a flared portion adjacent the inflow end of the prosthetic heart valve, wherein the flange includes a first braided mesh layer, a second braided mesh layer, and a layer of fabric between the first layer and the second layer wherein the plurality of cells includes an even number of cells arranged in a first circumferential row, four anchor arms being positioned in the first circumferential row so that a first pair of the anchor arms is symmetrical to a second pair of the anchor arms relative to a first plane bisecting the prosthetic heart valve, and a third pair of the anchor arms is symmetrical to a fourth pair of the anchor arms relative to a second plane orthogonal to the first plane.

12. The prosthetic heart valve of claim 11, wherein at least one of the anchor arms comprises a wire, the body portion of the anchor arm being formed by a center portion of the wire and the free end comprising two end portions of the wire on opposite sides of the center portion.

13. The prosthetic heart valve of claim 12, wherein at least one of the anchor arms includes an atraumatic end cap coupled to the two end portions of the wire.

14. The prosthetic heart valve of claim 11, wherein at least one of the anchor arms is sutured to the one cell.

15. The prosthetic heart valve of claim 11, wherein the one cell has a shape in the expanded condition of the stent and the body portion of at least one of the anchor arms has a shape in the expanded condition of the anchor arm that is substantially the same as the cell shape.

16. The prosthetic heart valve of claim 15, wherein the one cell is substantially diamond-shaped in the expanded condition of the stent and the body portion of the at least one of the anchor arms is substantially diamond-shaped in the expanded condition of the anchor arm.

17. The prosthetic heart valve of claim 11, wherein the flared portion of the flange has a first diameter in an expanded condition of the flange and the body portion of the flange has a second diameter in the expanded condition of the flange smaller than the first diameter.

18. The prosthetic heart valve of claim 11, wherein the flared portion of the flange terminates at an inflow end of the flange and the body portion of the flange terminates at an outflow end of the flange, the outflow end of the flange being positioned between the free end portion of at least one of the anchor arm and the body portion of the at least one anchor arm in the expanded condition of the stent.

* * * * *